(12) United States Patent
Chawla et al.

(10) Patent No.: US 11,371,096 B2
(45) Date of Patent: *Jun. 28, 2022

(54) BLOOD BIOMARKERS FOR APPENDICITIS AND DIAGNOSTICS METHODS USING BIOMARKERS

(71) Applicants: The George Washington University A Congressionally Chartered Not-For-Profit Corporation, Washington, DC (US); Astute Medical, Inc., San Diego, CA (US)

(72) Inventors: Lakhmir S. Chawla, McLean, VA (US); Timothy A. McCaffrey, Silver Spring, MD (US)

(73) Assignee: The George Washington University A Congressionally Chartered Not-For-Profit Corporation, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/521,213

(22) PCT Filed: Oct. 22, 2015

(86) PCT No.: PCT/US2015/057007
§ 371 (c)(1),
(2) Date: Apr. 21, 2017

(87) PCT Pub. No.: WO2016/065202
PCT Pub. Date: Apr. 28, 2016

(65) Prior Publication Data
US 2017/0356908 A1    Dec. 14, 2017

Related U.S. Application Data

(60) Provisional application No. 62/067,414, filed on Oct. 22, 2014.

(51) Int. Cl.
*C12Q 1/6883* (2018.01)
*G01N 33/68* (2006.01)
*G01N 33/566* (2006.01)
*G01N 33/84* (2006.01)

(52) U.S. Cl.
CPC ....... *C12Q 1/6883* (2013.01); *G01N 33/6893* (2013.01); *C12Q 2600/158* (2013.01); *G01N 33/566* (2013.01); *G01N 33/84* (2013.01); *G01N 2500/04* (2013.01); *G01N 2800/06* (2013.01)

(58) Field of Classification Search
CPC ............ C12Q 1/6883; C12Q 2600/158; G01N 33/6893; G01N 33/566; G01N 33/84; G01N 2800/56; G01N 2800/06; G01N 2500/04; G01N 33/53
See application file for complete search history.

(56) References Cited

U.S. PATENT DOCUMENTS

| 2012/0028268 | A1 | 2/2012 | Kentsis et al. | |
| 2013/0122528 | A1 | 5/2013 | Tyrell et al. | |
| 2013/0171670 | A1 | 7/2013 | Bar-Or et al. | |
| 2014/0135225 | A1* | 5/2014 | Crow ................ | C12Q 1/6883 506/9 |
| 2014/0220580 | A1* | 8/2014 | Brown ............. | G01N 33/57434 435/6.12 |

FOREIGN PATENT DOCUMENTS

| SU | 1 446 526 A1 | 12/1988 |
| WO | WO-2004-059293 A2 | 7/2004 |

OTHER PUBLICATIONS

Murphy, Mucosal Immunology | vol. 1 No. 4 | Jul. 2008 (Year: 2008).*
Yamaguchi (2009;58:192-7).*
Kanmura et al (Inflam Bowel Dis, 2009;vol. 15, No. 6 p. 909-917).*
Grupp et al. (peritoneal Dialysis International vol. 27. pp. 654-662).*
Xin et al (Fangshe Mianyixue Zazhi 2012; vol. 25, issue 1 pp. 47-48, Abstract.*
Weirong et al. (Fangshe Mianyixue Zazhi 2012;25(6),655-666 Abstract).*
International Search Report in International Application No. PCT/US2015/057007, dated Jan. 29, 2016.
Ahn, "LOCAT (low-dose computed tomography for appendicitis trial) comparing clinical outcomes following low- vs standard-dose computed tomography as the first-line imaging test in adolescents and young adults with suspected acute appendicitis: study protocol for a randomized controlled trial", Ahn Trials (2014), vol. 15, No. 28 (10 pages).
Andersson et al., "Can new inflammatory markers improve the diagnosis of acute appendicitis?",World J Surg (2014), vol. 38, pp. 2777-2783.
Arlt et al., "Characteristic changes in microbial community composition and expression of innate immune genes in acute appendicitis", Innate Immun (2015), vol. 21, No. 1, pp. 30-41.
Baines et al., "Sputum gene expression signature of 6 biomarkers discriminates asthma inflammatory phenotypes", J Allergy Clin Immunol, vol. 133, pp. 997-1007.
Bhuiya et al., "Emergency Department visits for chest pain and abdominal pain: United States, 1999-2008", CDC, NCHS Data Brief No. 43, Sep. 2010.

(Continued)

Primary Examiner — Ellen J Marcsisin
(74) Attorney, Agent, or Firm — Kory D. Christensen

(57) ABSTRACT

The invention relates to methods and kits for diagnosing and/or treating appendicitis in a subject, comprising performing one or more assays configured to detect one or more biomarkers on a body fluid sample obtained from the subject to provide one or more assay result(s) and correlating the assay result(s) to the occurrence or nonoccurrence of appendicitis in the subject or likelihood of the future outcome to the subject.

3 Claims, 7 Drawing Sheets

(56) References Cited

OTHER PUBLICATIONS

Charfi et al., "Histopathological findings in appendectomy specimens: a study of 24,697 cases", Int J Colorectal Dis (2014), vol. 29, pp. 1009-1012.
Collins et al., "The accuracy of pre-appendectomy computed tomography with histopathological correlation: a clinical audit, case discussion and evaluation of the literature", Emerg Radiol (2014), vol. 21, pp. 589-595.
Congiu et al., "Expression of common housekeeping genes is affected by disease in human hepatitis C virus-infected liver", Liver Int (2011), vol. 31, pp. 386-390.
Derenzini et al., "Spatial redistribution of ribosomal chromatin in the fibrillar centres of human circulating lymphocytes after stimulation of transcription", Exp Cell Res (1987), vol. 170, pp. 31-41.
Drake et al., "Progress in the diagnosis of appendicitis: a report from Washington State's Surgical Care and Outcomes Assessment Program", Ann Surg (2012), vol. 256, pp. 586-594.
D'Souza et al., "Bilirubin; a diagnostic marker for appendicitis", Int J Surg (2013), vol. 11, pp. 1114-1117.
Guinane et al., Microbial composition of human appendices from patients following appendectomy. MBio (2013), vol. 4, Issue 1 (6 pages).
Haaf et al., "Quantitative determination of rDNA transcription units in vertebrate cells", Exp Cell Res (1991), vol. 193, pp. 78-86.
Huang et al., "Systematic and integrative analysis of large gene lists using DAVID bioinformatics resources", Nat Protoc (2009), vol. 4, pp. 44-57.
Huang et al., "The identification of novel proteins that interact with the GLP-1 receptor and restrain its activity", Mol Endocrinol (2013), vol. 27, pp. 1550-1563.
Huckins et al., "A novel biomarker panel to rule out acute appendicitis in pediatric patients with abdominal pain", Am J Emerg Med (2013), vol. 31, pp. 1368-1375.
Jackson et al., "Culture-independent evaluation of the appendix and rectum microbiomes in children with and without appendicitis", PLoS One (2014), vol. 9, pp. e95414.
Kaya et al., "The diagnostic value of D-dimer, procalcitonin and CRP in acute appendicitis", Int J Med Sci (2012), vol. 9, pp. 909-915.
Keyzer et al., "Acute Appendicitis: Comparison of Low-Dose and Standard-Dose Unenhanced Multi-Detector Row CT", Radiology (2004), vol. 232, pp. 164-172.
Kim et al., "Acute Appendicitis in Young Adults: Low- versus Standard-Radiation-Dose Contrast-enhanced Abdominal CT for Diagnosis", Radiology (2011), vol. 260, pp. 437-445.
Kirkil et al., "Appendicitis scores may be useful in reducing the costs of treatment for right lower quadrant pain", Ulus Travma Acil Cerrahi Derg (2013), vol. 19, pp. 13-19.
Kubo et al., "Analysis of genes induced in peripheral nerve after axotomy using cDNA microarrays", J Neurochem (2002), vol. 82, pp. 1129-1136.
Memon et al., "Acute appendicitis: diagnostic accuracy of Alvarado scoring system", Asian J Surg (2013), vol. 36, pp. 144-149.
Miglioretti et al., "Pediatric Computed Tomography and Associated Radiation Exposure and Estimated Cancer Risk", JAMA Pediatr (2013), vol. 167, pp. 700-707.
Ohkusa et al., "Induction of experimental ulcerative colitis by Fusobacterium varium isolated from colonic mucosa of patients with ulcerative colitis", Gut (2003), vol. 52, pp. 79-83.
Peyyala et al., "Oral microbial biofilm stimulation of epithelial cell responses", Cytokine (2012), vol. 58, pp. 65-72.
Pike et al., "A novel hypothesis for an alkaline phosphatase 'rescue' mechanism in the hepatic acute phase immune response", Biochim Biophys Acta (2013), vol. 1832, pp. 2044-2056.
Poortinga et al., "c-MYC coordinately regulates ribosomal gene chromatin remodeling and Pol I availability during granulocyte differentiation", Nucleic Acids Res (2011), vol. 39, pp. 3267-3281.
Poortman et al., "Improving Diagnosis of Acute Appendicitis: Results of a Diagnostic Pathway with Standard Use of Ultrasonography Followed by Selective Use of CT", Journal of the American College of Surgeons (2009), vol. 208, pp. 434-441.
Ramdass et al., "Association between the appendix and the fecalith in adults", Can J Surg (2015), vol. 58, pp. 10-14.
Remacha et al., "Ribosomal acidic phosphoproteins P1 and P2 are not required for cell viability but regulate the pattern of protein expression in Saccharomyces cerevisiae". Mol Cell Biol (1995), vol. 15, pp. 4754-4762.
Rosen et al., "ACR Appropriateness Criteria® Right Lower Quadrant Pain-Suspected Appendicitis", Journal of the American College of Radiology (2011), vol. 8, pp. 749-755.
Seetahal et al., "Negative appendectomy: a 10-year review of a nationally representative sample", The American Journal of Surgery (2011), vol. 201, pp. 433-437.
Seo et al., "Diagnosis of Acute Appendicitis With Sliding Slab Ray-Sum Interpretation of Low-Dose Unenhanced CT and Standard-Dose IV Contrast-Enhanced CT Scans", American Journal of Roentgenology (2009), vol. 193, pp. 96-105.
Shiue et al., "Myc-induced anchorage of the rDNA IGS region to nucleolar matrix modulates growth-stimulated changes in higher-order rDNA architecture", Nucleic Acids Res (2014), vol. 42, pp. 5505-5517.
Subrahmanyam et al., "RNA expression patterns change dramatically in human neutrophils exposed to bacteria", Blood (2001), vol. 97, pp. 2457-2468.
Swidsinski et al., "Acute appendicitis is characterised by local invasion with Fusobacterium nucleatum/necrophorum", Gut (2011), vol. 60, pp. 34-40.
Teixeira "Appendicitis: changing perspectives", Adv Surg (2013), vol. 47, pp. 119-140.
Uemura et al., "Overexpression of ribosomal RNA in prostate cancer is common but not linked to rDNA promoter hypomethylation", Oncogene (2012), vol. 31, pp. 1254-1263.
Wai et al., "The utility of the emergency department observation unit for children with abdominal pain", Pediatr Emerg Care (2013), vol. 29, pp. 574-578.
Watson et al., "Increased prokineticin 2 expression in gut inflammation: role in visceral pain and intestinal ion transport", Neurogastroenterol Motil (2012), vol. 24, pp. 65-75, e12.
Wu et al., "Diagnostic role of procalcitonin in patients with suspected appendicitis", World J Surg (2012), vol. 36, pp. 1744-1749.
Zeillemaker et al., "Peritoneal interleukin-8 in acute appendicitis", J Surg Res (1996), vol. 62, pp. 273-277.
Zhang et al., "Identification and analysis of over 2000 ribosomal protein pseudogenes in the human genome", Genome Res (2002), vol. 12, pp. 1466-1482.
Zhong et al., "Acute appendicitis in children is associated with an abundance of bacteria from the phylum Fusobacteria", J Pediatr Surg (2014), vol. 49, pp. 441-446.
European Office Action, Application No. 19 153 228.2, dated Jul. 6, 2021.
Anonymous: "Platform GPL 10558—Illumina HumanHT-12 V4.0 expression leadchip," Jun. 17, 2010 (17, 2010), Retrieved from the Internet: URL:https:/www.ncbi.nlm.nih.gov/geo/query/acc.cgi?acc=GPL10558 [retrieved on May 18, 2020] (2 pages).
"Data Sheet: Gene Expression Array-Based Gene Expression Analysis," Illumina, Jan. 1, 2011 (Jan. 1, 2011), Retrieved from the Internet: URL:http://support.illumina.com/content/dam/illumina-marketing/documents/products/datasheets/datasheet_gene_exp_analysis.pdf (retreived on Mar. 18, 2016).
Greenbaum D et al: "Comparing Protein Abundance and MRNA Expression Levels on a Genomic Scale," Genome Biology (Online), Biomed Central Ltd, GB, vol. 40, No. 9, Jan. 1, 2003 (Jan. 1, 2003,) pp. 117.01-117.08.
Li et al.: "Determination of plasma beta-defensin-2 concentration in patients with acute appendicitis and its clinical significance," Fangshe Mianyixue Zashi, vol. 25, No. 1, Jan. 1, 2012 (Jan. 1, 2012), pp. 47-48.

\* cited by examiner

■ = Abdominal discomfort
▲ = Appendicitis

BLOOD BIOMARKERS FOR APPENDICITIS AND DIAGNOSTICS METHODS USING BIOMARKERS

CROSS-REFERENCE OF RELATED APPLICATION

This application is a U.S. National Phase Application of PCT/US2015/057007, filed Oct. 22, 2015, which claims priority to U.S. Provisional Application No. 62/067,414, filed Oct. 22, 2014, the entire contents of which are hereby incorporated by reference.

BACKGROUND

1. Technical Field

The field of the currently claimed embodiments of this invention relate to methods and kits for assessing and treating abdominal discomfort/pain (the terms abdominal pain and abdominal discomfort will be used interchangeably throughout) and appendicitis in a subject, and more particularly to assessing and treating abdominal discomfort and appendicitis in a subject using the analysis of biomarkers isolated from the subject.

2. Discussion of Related Art

Abdominal pain is a major cause of hospital visits, accounting for about 10% of 62 million visits per year by adults who present at an emergency department (ED) for non-injury causes [1]. Acute appendicitis is one of the most common causes of abdominal pain and results in nearly 750,000 ED visits with approximately 250,000 appendectomies performed annually. Globally, a small but significant portion of the operations are "negative appendectomies", resulting in the removal of a non-inflamed appendix due to misdiagnosis [2-4], reported as high as 17-28% outside the US and Western Europe [5,6].

Prior to the widespread availability of computed tomography (CT) scans, the accurate diagnosis of appendicitis could be challenging, and in places where CT is still not available, the Alvarado score of clinical characteristics is a widely used diagnostic tool [5,6]. Currently in the United States, CT scanning is the 'gold standard' for the diagnosis of appendicitis, with magnetic resonance imaging (MRI) being a reasonable alternative in pregnant women [7], and ultrasound sonography being an acceptable alternative for preliminary diagnostics to avoid radiation [8]. While CT is the most sensitive and specific diagnostic tool for appendicitis [9,10], and used in almost 98% of patients undergoing appendectomy in the US [11], CT scanning carries a significant radiation exposure, and epidemiologic data suggest that radiation exposure can increase the risk of developing a future malignancy [12]. This issue is of particular concern in children because they are more sensitive to the hazards of radiation, they are among the most common patients to present to the ED with abdominal pain, and have the highest rate of misdiagnosis [10,13]. In an attempt to reduce the damaging effect of CT scans, several clinical trials are examining the diagnostic utility of lower doses of radiation, primarily in children [14-16].

In order to utilize CT scanning more appropriately, and to improve diagnosis in areas where CT scans are unavailable, blood biomarkers were identified that serve as a preliminary safe and rapid test to help identify patients with appendicitis. Genome-wide profiling of RNA transcripts in whole blood RNA of patients presenting at the ED for abdominal pain was conducted, resulting in confirmed appendicitis versus other abdominal abnormalities.

Some embodiments of the present invention include methods and kits for assessing and treating abdominal discomfort and appendicitis in a subject, and more particularly to assessing and treating abdominal discomfort and appendicitis in a subject using the analysis of biomarkers isolated from the subject.

SUMMARY

Embodiments of the invention include methods of diagnosing appendicitis in a subject, or assigning a likelihood of a future outcome to a subject diagnosed with appendicitis, comprising performing one or more assays configured to detect one or more biomarkers selected from the group consisting of Chemokine C-X-C receptor 1, Interleukin 8 receptor ß, Fc frag of IgG receptor IIIb (CD16b), MHC class II DR beta 5, Leukocyte IgG-like receptor A3, Defensin alpha 1, Defensin alpha 1B, Defensin alpha 3, 18S ribosomal RNA, CDC14A, 28S ribosomal RNA, 60S acidic ribosomal protein P1, 40S ribosomal protein S26, Ribosomal protein L23, Ribosomal protein L37a, Ribosomal protein S28, Alkaline phosphatase, Carbonic anhydrase IV, Neuroblastoma breakpoint family 10, Ninjurin 1, Prokineticin 2, Superoxide dismutase 2, LOC100129902, LOC100131205, LOC100131905, LOC100132291, LOC100132394, LOC100132742, LOC100134364, LOC391370, LOC646785, LOC644191 and C5orf32 on a body fluid sample obtained from the subject to provide one or more assay result(s); and correlating the assay result(s) to the occurrence or nonoccurrence of appendicitis in the subject or likelihood of the future outcome to the subject.

Embodiments of the invention include methods for evaluating biomarker levels in a body fluid sample, comprising obtaining a body fluid sample from a subject selected for evaluation based on a determination that the subject is experiencing symptoms indicative of possible acute appendicitis; and performing one or more analyte binding assays configured to detect one or more biomarkers selected from the group consisting of Chemokine C-X-C receptor 1, Interleukin 8 receptor ß, Fc frag of IgG receptor IIIb (CD16b), MHC class II DR beta 5, Leukocyte IgG-like receptor A3, Defensin alpha 1, Defensin alpha 1B, Defensin alpha 3, 18S ribosomal RNA, CDC14A, 28S ribosomal RNA, 60S acidic ribosomal protein P1, 40S ribosomal protein S26, Ribosomal protein L23, Ribosomal protein L37a, Ribosomal protein S28, Alkaline phosphatase, Carbonic anhydrase IV, Neuroblastoma breakpoint family 10, Ninjurin 1, Prokineticin 2, Superoxide dismutase 2, LOC100129902, LOC100131205, LOC100131905, LOC100132291, LOC100132394, LOC100132742, LOC100134364, LOC391370, LOC646785, LOC644191 and C5orf32 by introducing the body fluid sample obtained from the subject into an assay instrument which (i) contacts the body fluid sample with one or more binding reagents corresponding to the biomarker(s) being assayed, wherein each biomarker which is assayed binds to its respective specific binding reagent in an amount related to its concentration in the body fluid sample, (ii) generates one or more assay results indicative of binding of each biomarker which is assayed to its respective specific binding reagent; and (iii) displays the one or more assay results as a quantitative result in a human-readable form.

Embodiments of the invention include systems for evaluating biomarker levels, comprising a plurality of reagents which specifically bind for detection a plurality of biomarkers selected from the group consisting of Chemokine C-X-C receptor 1, Interleukin 8 receptor ß, Fc frag of IgG receptor IIIb (CD16b), MHC class II DR beta 5, Leukocyte IgG-like receptor A3, Defensin alpha 1, Defensin alpha 1B, Defensin alpha 3, 18S ribosomal RNA, CDC14A, 28S ribosomal RNA, 60S acidic ribosomal protein P1, 40S ribosomal protein S26, Ribosomal protein L23, Ribosomal protein L37a, Ribosomal protein S28, Alkaline phosphatase, Carbonic anhydrase IV, Neuroblastoma breakpoint family 10, Ninjurin 1, Prokineticin 2, Superoxide dismutase 2, LOC100129902, LOC100131205, LOC100131905, LOC100132291, LOC100132394, LOC100132742, LOC100134364, LOC391370, LOC646785, LOC644191 and C5orf32; an assay instrument configured to (i) receive a body fluid sample, (ii) contact the plurality of reagents with the body fluid sample and (iii) generate and quantitatively display in human readable form one or more assay results indicative of binding of each biomarker which is assayed to a respective specific binding reagent in the plurality of reagents.

Embodiments of the invention include uses of one or more reagents which specifically bind for detection one or more biomarkers selected from the group consisting of Chemokine C-X-C receptor 1, Interleukin 8 receptor ß, Fc frag of IgG receptor IIIb (CD16b), MHC class II DR beta 5, Leukocyte IgG-like receptor A3, Defensin alpha 1, Defensin alpha 1B, Defensin alpha 3, 18S ribosomal RNA, CDC14A, 28S ribosomal RNA, 60S acidic ribosomal protein P1, 40S ribosomal protein S26, Ribosomal protein L23, Ribosomal protein L37a, Ribosomal protein S28, Alkaline phosphatase, Carbonic anhydrase IV, Neuroblastoma breakpoint family 10, Ninjurin 1, Prokineticin 2, Superoxide dismutase 2, LOC100129902, LOC100131205, LOC100131905, LOC100132291, LOC100132394, LOC100132742, LOC100134364, LOC391370, LOC646785, LOC644191 and C5orf32 for the diagnosis of appendicitis.

Embodiments of the invention include uses of one or more biomarkers selected from the group consisting of Chemokine C-X-C receptor 1, Interleukin 8 receptor ß, Fc frag of IgG receptor IIIb (CD16b), MHC class II DR beta 5, Leukocyte IgG-like receptor A3, Defensin alpha 1, Defensin alpha 1B, Defensin alpha 3, 18S ribosomal RNA, CDC14A, 28S ribosomal RNA, 60S acidic ribosomal protein P1, 40S ribosomal protein S26, Ribosomal protein L23, Ribosomal protein L37a, Ribosomal protein S28, Alkaline phosphatase, Carbonic anhydrase IV, Neuroblastoma breakpoint family 10, Ninjurin 1, Prokineticin 2, Superoxide dismutase 2, LOC100129902, LOC100131205, LOC100131905, LOC100132291, LOC100132394, LOC100132742, LOC100134364, LOC391370, LOC646785, LOC644191 and C5orf32 for the diagnosis of appendicitis.

BRIEF DESCRIPTION OF THE DRAWINGS

Further objectives and advantages will become apparent from a consideration of the description, drawings, and examples.

DETAILED DESCRIPTION

Figure 1:
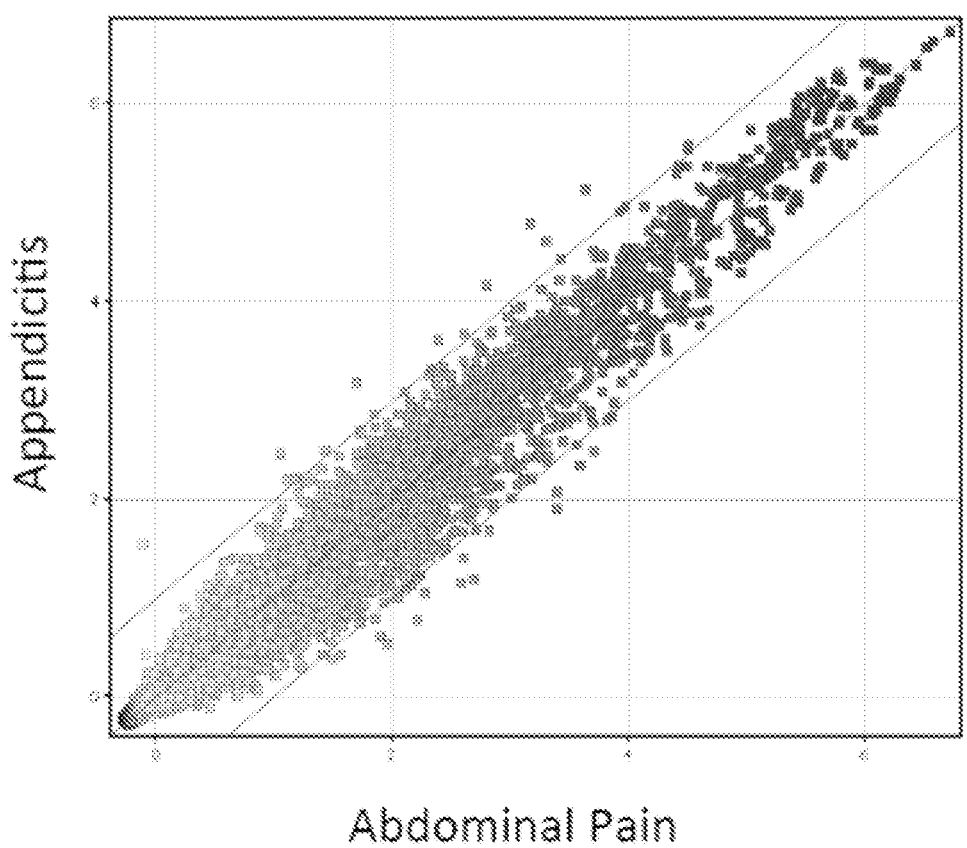
FIG. 1 is a scatterplot of the expression patterns in 2 groups of patients.

In some embodiments, the invention relates to a method of diagnosing appendicitis in a subject, or assigning a likelihood of a future outcome to a subject diagnosed with appendicitis, comprising performing one or more assays configured to detect one or more biomarkers selected from the group consisting of Chemokine C-X-C receptor 1, Interleukin 8 receptor ß, Fc frag of IgG receptor IIIb (CD16b), MHC class II DR beta 5, Leukocyte IgG-like receptor A3, Defensin alpha 1, Defensin alpha 1B, Defensin alpha 3, 18S ribosomal RNA, CDC14A, 28S ribosomal RNA, 60S acidic ribosomal protein P1, 40S ribosomal protein S26, Ribosomal protein L23, Ribosomal protein L37a, Ribosomal protein S28, Alkaline phosphatase, Carbonic anhydrase IV, Neuroblastoma breakpoint family 10, Ninjurin 1, Prokineticin 2, Superoxide dismutase 2, LOC100129902, LOC100131205, LOC100131905, LOC100132291, LOC100132394, LOC100132742, LOC100134364, LOC391370, LOC646785, LOC644191 and C5orf32 on a body fluid sample obtained from the subject to provide one or more assay result(s); and correlating the assay result(s) to the occurrence or nonoccurrence of appendicitis in the subject or likelihood of the future outcome to the subject.

In some embodiments, the invention relates to the method above, wherein the performing step comprises introducing the body fluid sample obtained from the subject into an assay instrument which (i) contacts the body fluid sample with one or more binding reagents corresponding to the biomarker(s) being assayed, wherein each biomarker which is assayed binds to its respective specific binding reagent in an amount related to its concentration in the body fluid sample, (ii) generates one or more assay results indicative of binding of each biomarker which is assayed to its respective specific binding reagent; and (iii) displays the one or more assay results as a quantitative result in a human-readable form.

In some embodiments, the invention relates to the method above, wherein the specific binding reagent is an antibody.

In some embodiments, the invention relates to the method above, wherein the one or more assays are sandwich assays.

In some embodiments, the invention relates to the method above, wherein the correlating step comprises comparing the assay result(s) or a value derived therefrom to a threshold selected in a population study to separate the population into a first subpopulation at higher predisposition for the occurrence of appendicitis or the future outcome, and a second subpopulation at lower predisposition for the occurrence of appendicitis or the future outcome relative to the first subpopulation.

In some embodiments, the invention relates to the method above, and further comprises treating the subject based on the predetermined subpopulation of individuals to which the patient is assigned, wherein if the patient is in the first subpopulation, the treatment comprises treating the subject for appendicitis or the future outcome.

In some embodiments, the invention relates to the method above, wherein the future outcome is mortality.

In some embodiments, the invention relates to the method above, wherein the subject is being evaluated for abdominal pain.

In some embodiments, the invention relates to the method above, wherein the correlating step comprises determining the concentration of each biomarker which is assayed, and individually comparing each biomarker concentration to a corresponding threshold level for that biomarker.

In some embodiments, the invention relates to the method above, wherein the assay instrument comprises a processing system configured to perform the correlating step and output the assay result(s) or a value derived therefrom in human readable form.

In some embodiments, the invention relates to the method above, wherein a plurality of the biomarkers are measured, wherein the assay instrument performs the correlating step, which comprises determining the concentration of each of the plurality of biomarkers, calculating a single value based on the concentration of each of the plurality of biomarkers, comparing the single value to a corresponding threshold level and displaying an indication of whether the single value does or does not exceed its corresponding threshold in a human-readable form.

In some embodiments, the invention relates to the method above, wherein method provides a sensitivity or specificity of at least 0.7 for the identification of appendicitis when compared to normal subjects.

In some embodiments, the invention relates to the method above, wherein method provides a sensitivity or specificity of at least 0.7 for the identification of appendicitis when compared to subjects exhibiting symptoms that mimic appendicitis symptoms.

In some embodiments, the invention relates to the method above, wherein the sample is selected from the group consisting of blood, serum, and plasma.

In some embodiments, the invention relates to the method above, wherein the sample is urine.

In some embodiments, the invention relates to a method for evaluating biomarker levels in a body fluid sample, comprising obtaining a body fluid sample from a subject selected for evaluation based on a determination that the subject is experiencing symptoms indicative of possible acute appendicitis; and performing one or more analyte binding assays configured to detect one or more biomarkers selected from the group consisting of Chemokine C-X-C receptor 1, Interleukin 8 receptor ß, Fc frag of IgG receptor IIIb (CD16b), MHC class II DR beta 5, Leukocyte IgG-like receptor A3, Defensin alpha 1, Defensin alpha 1B, Defensin alpha 3, 18S ribosomal RNA, CDC14A, 28S ribosomal RNA, 60S acidic ribosomal protein P1, 40S ribosomal protein S26, Ribosomal protein L23, Ribosomal protein L37a, Ribosomal protein S28, Alkaline phosphatase, Carbonic anhydrase IV, Neuroblastoma breakpoint family 10, Ninjurin 1, Prokineticin 2, Superoxide dismutase 2, LOC100129902, LOC100131205, LOC100131905, LOC100132291, LOC100132394, LOC100132742, LOC100134364, LOC391370, LOC646785, LOC644191 and C5orf32 by introducing the body fluid sample obtained from the subject into an assay instrument which (i) contacts the body fluid sample with one or more binding reagents corresponding to the biomarker(s) being assayed, wherein each biomarker which is assayed binds to its respective specific binding reagent in an amount related to its concentration in the body fluid sample, (ii) generates one or more assay results indicative of binding of each biomarker which is assayed to its respective specific binding reagent; and (iii) displays the one or more assay results as a quantitative result in a human-readable form.

In some embodiments, the invention relates to the method above, wherein the assay result(s) are displayed as a concentration of each biomarker which is assayed.

In some embodiments, the invention relates to the method above, wherein the assay instrument further individually compares each biomarker concentration to a corresponding threshold level for that biomarker, and displays an indication of whether each biomarker does or does not exceed its corresponding threshold in a human-readable form.

In some embodiments, the invention relates to the method above, wherein a plurality of the biomarkers are measured, and wherein the assay results(s) comprise a single value calculated using a function that converts the concentration of each of the plurality of biomarkers into a single value.

In some embodiments, the invention relates to the method above, wherein the assay instrument further compares the single value to a corresponding threshold level and displays an indication of whether the single value does or does not exceed its corresponding threshold in a human-readable form.

In some embodiments, the invention relates to the method above, wherein the subject is selected for evaluation of a mortality risk within a period selected from the group consisting of 21 days, 14 days, 7 days, 5 days, 96 hours, 72 hours, 48 hours, 36 hours, 24 hours, and 12 hours.

In some embodiments, the invention relates to the method above, wherein the plurality of assays are immunoassays performed by (i) introducing the body fluid sample into an assay device comprising a plurality of antibodies, at least one of which binds to each biomarker which is assayed, and (ii) generating an assay result indicative of binding of each biomarker to its respective antibody.

In some embodiments, the invention relates to a system for evaluating biomarker levels, comprising a plurality of reagents which specifically bind for detection a plurality of biomarkers selected from the group consisting of Chemokine C-X-C receptor 1, Interleukin 8 receptor ß, Fc frag of IgG receptor IIIb (CD16b), MHC class II DR beta 5, Leukocyte IgG-like receptor A3, Defensin alpha 1, Defensin alpha 1B, Defensin alpha 3, 18S ribosomal RNA, CDC14A, 28S ribosomal RNA, 60S acidic ribosomal protein P1, 40S ribosomal protein S26, Ribosomal protein L23, Ribosomal protein L37a, Ribosomal protein S28, Alkaline phosphatase, Carbonic anhydrase IV, Neuroblastoma breakpoint family 10, Ninjurin 1, Prokineticin 2, Superoxide dismutase 2, LOC100129902, LOC100131205, LOC100131905, LOC100132291, LOC100132394, LOC100132742, LOC100134364, LOC391370, LOC646785, LOC644191 and C5orf32; an assay instrument configured to (i) receive a body fluid sample, (ii) contact the plurality of reagents with the body fluid sample and (iii) generate and quantitatively display in human readable form one or more assay results indicative of binding of each biomarker which is assayed to a respective specific binding reagent in the plurality of reagents.

In some embodiments, the invention relates to the system above, wherein the reagents comprise a plurality of antibodies, at least one of which binds to each of the biomarkers which are assayed.

In some embodiments, the invention relates to the system above, wherein assay instrument comprises an assay device and an assay device reader, wherein the plurality of antibodies are immobilized at a plurality of predetermined locations within the assay device, wherein the assay device is configured to receive the body fluid sample such that the body fluid sample contacts the plurality of predetermined locations, and wherein the assay device reader interrogates the plurality of predetermined locations to generate the assay results.

In some embodiments, the invention relates to a use of one or more reagents which specifically bind for detection one or more biomarkers selected from the group consisting of Chemokine C-X-C receptor 1, Interleukin 8 receptor ß, Fc frag of IgG receptor IIIb (CD16b), MHC class II DR beta 5, Leukocyte IgG-like receptor A3, Defensin alpha 1, Defensin alpha 1B, Defensin alpha 3, 18S ribosomal RNA, CDC14A, 28S ribosomal RNA, 60S acidic ribosomal protein P1, 40S ribosomal protein S26, Ribosomal protein L23, Ribosomal protein L37a, Ribosomal protein S28, Alkaline phosphatase, Carbonic anhydrase IV, Neuroblastoma breakpoint family 10, Ninjurin 1, Prokineticin 2, Superoxide dismutase 2, LOC100129902, LOC100131205, LOC100131905, LOC100132291, LOC100132394, LOC100132742, LOC100134364, LOC391370, LOC646785, LOC644191 and C5orf32 for the diagnosis of appendicitis.

In some embodiments, the invention relates to a use of one or more biomarkers selected from the group consisting of Chemokine C-X-C receptor 1, Interleukin 8 receptor ß, Fc frag of IgG receptor IIIb (CD16b), MHC class II DR beta 5, Leukocyte IgG-like receptor A3, Defensin alpha 1, Defensin alpha 1B, Defensin alpha 3, 18S ribosomal RNA, CDC14A, 28S ribosomal RNA, 60S acidic ribosomal protein P1, 40S ribosomal protein S26, Ribosomal protein L23, Ribosomal protein L37a, Ribosomal protein S28, Alkaline phosphatase, Carbonic anhydrase IV, Neuroblastoma breakpoint family 10, Ninjurin 1, Prokineticin 2, Superoxide dismutase 2, LOC100129902, LOC100131205, LOC100131905, LOC100132291, LOC100132394, LOC100132742, LOC100134364, LOC391370, LOC646785, LOC644191 and C5orf32 for the diagnosis of appendicitis.

Definitions

To facilitate an understanding of the present invention, a number of terms and phrases are defined below.

As used herein, the singular forms "a", "an", and "the" include plural forms unless the context clearly dictates otherwise. Thus, for example, reference to "a binding agent" includes reference to more than one binding agent.

The terms "diagnostic" and "diagnosis" refer to identifying the presence or nature of a pathologic condition and includes identifying patients who are at risk of developing a specific disease or disorder. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay, are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

The terms "detection", "detecting" and the like, may be used in the context of detecting biomarkers, or of detecting a disease or disorder (e.g., when positive assay results are obtained). In the latter context, "detecting" and "diagnosing" are considered synonymous.

The terms "subject", "patient" or "individual" generally refer to a human, although the methods of the invention are not limited to humans, and should be useful in other mammals (e.g., cats, dogs, etc.).

"Sample" is used herein in its broadest sense. A sample may comprise a bodily fluid including blood, serum, plasma, tears, aqueous and vitreous humor, spinal fluid, urine, and saliva; a soluble fraction of a cell or tissue preparation, or media in which cells were grown. Means of obtaining suitable biological samples are known to those of skill in the art.

An "antibody" is an immunoglobulin molecule that recognizes and specifically binds to a target, such as a protein, polypeptide, peptide, carbohydrate, polynucleotide, lipid, etc., through at least one antigen recognition site within the variable region of the immunoglobulin molecule. As used herein, the term is used in the broadest sense and encompasses intact polyclonal antibodies, intact monoclonal antibodies, antibody fragments (such as Fab, Fab', F(ab')$_2$, and Fv fragments), single chain Fv (scFv) mutants, multispecific antibodies such as bispecific antibodies generated from at least two intact antibodies, hybrid antibodies, fusion proteins comprising an antibody portion, and any other modified immunoglobulin molecule comprising an antigen recognition site so long as the antibodies exhibit the desired biological activity. An antibody may be of any the five major classes of immunoglobulins: IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies may be naked or conjugated to other molecules such as toxins, radioisotopes, etc.

The term "antibody fragments" refers to a portion of an intact antibody. Examples of antibody fragments include, but are not limited to, linear antibodies; single-chain antibody molecules; Fc or Fc' peptides, Fab and Fab fragments, and multispecific antibodies formed from antibody fragments.

"Hybrid antibodies" are immunoglobulin molecules in which pairs of heavy and light chains from antibodies with different antigenic determinant regions are assembled together so that two different epitopes or two different antigens may be recognized and bound by the resulting tetramer.

"Isolated" in regard to cells, refers to a cell that is removed from its natural environment and that is isolated or separated, and is at least about 30%, 50%, 75%, and 90% free from other cells with which it is naturally present, but which lack the marker based on which the cells were isolated.

For use in the diagnostic and therapeutic applications described herein, kits are also within the scope of the invention. Such kits can comprise a carrier, package or container that is compartmentalized to receive one or more containers such as vials, tubes, and the like, each of the container(s) comprising one of the separate elements to be used in the method. For example, the container(s) can comprise a probe that is or can be detectably labeled. The probe can be an antibody or polynucleotide specific for a biomarker of interest. Alternatively, the kit can comprise a mass spectrometry (MS) probe. The kit can also include containers containing nucleotide(s) for amplification or silencing of a target nucleic acid sequence, and/or a container comprising a reporter means, such as a biotin-binding protein, e.g., avidin or streptavidin, bound to a detectable label, e.g., an enzymatic, florescent, or radioisotope label. The kit can include all or part of the amino acid sequence of the biomarker, or a nucleic acid molecule that encodes such amino acid sequences.

The kit of the invention will typically comprise the container described above and one or more other containers comprising materials desirable from a commercial and user standpoint, including buffers, diluents, filters, needles, syringes, and package inserts with instructions for use. In addition, a label can be provided on the container to indicate that the composition is used for a specific therapeutic or non-therapeutic application, and can also indicate directions for either in vivo or in vitro use, such as those described above. Directions and or other information can also be included on an insert which is included with the kit.

Polynucleotides may be prepared using any of a variety of techniques known in the art. The polynucleotide sequences selected as probes (and bind to the biomarkers of interest) should be sufficiently long and sufficiently unambiguous that false positives are minimized. The polynucleotide is preferably labeled such that it can be detected upon hybridization to DNA and/or RNA in the assay being screened. Methods of labeling are well known in the art, and include the use of radiolabels, such as 32P-labeled ATP, biotinylation, fluorescent groups or enzyme labeling. Hybridization conditions, including moderate stringency and high stringency, are well known in the art.

Polynucleotide variants may generally be prepared by any method known in the art, including chemical synthesis by, for example, solid phase phosphoramidite chemical synthesis. Modifications in a polynucleotide sequence may also be introduced using standard mutagenesis techniques, such as oligonucleotide-directed site-specific mutagenesis. Alternatively, RNA molecules may be generated by in vitro or in vivo. Certain portions may be used to prepare an encoded polypeptide.

Any polynucleotide may be further modified to increase stability in vive and/or in vitro for improved activity and/or storage. Possible modifications include, but are not limited to, the addition of flanking sequences at the 5' and/or 3' ends; the use of phosphorothioate or 2' O-methyl rather than phosphodiesterase linkages in the backbone; and/or the inclusion of nontraditional bases such as inosine, queosine and wybutosine, as well as acetyl-methyl-, thio- and other modified forms of adenine, cytidine, guanine, thymine and uridine.

Polynucleotides and/or antibodies specific to biomarkers of interest can be conjugated to detectable markers to a second molecule. Suitable detectable markers include, but are not limited to, a radioisotope, a fluorescent compound, a bioluminescent compound, chemiluminescent compound, a metal chelator or an enzyme. A second molecule for conjugation can be selected in accordance with the intended use. For example, for therapeutic use, the second molecule can be a toxin or therapeutic agent. Further, bi-specific antibodies specific for two or more biomarkers may be generated using methods generally known in the art. Homodimeric antibodies may also be generated by cross-linking techniques known in the art.

EXAMPLES

The following examples help explain some concepts of the current invention. However, the general concepts of the current invention are not limited to the particular examples.

Example 1: Acute Appendicitis: Transcript Profiling of Blood Identifies Promising Biomarkers and Potential Underlying Processes Materials and Methods Subjects.

Ethics statement: The protocol of this observational study was approved by the Institutional Review Board of The George Washington University, and all subjects gave informed consent. From a cohort of 270 patients presenting to the ED for various reasons, a subset of 40 subjects with a principal complaint of abdominal pain, and who met inclusion/exclusion criteria, were identified, and divided into a discovery set of 20 patients, and a validation set of 20 patients for transcript profiling of whole blood RNA by microarray.

Discovery Set: For the discovery set, we employed 20 subjects who presented to the ED who were undergoing CT scanning. In order to meet criteria, the patient undergoing the CT scan must have had appendicitis suspected in the differential diagnosis. Appendicitis Patients: Patients with appendicitis were diagnosed by CT scanning (n=11), and had research blood samples drawn by venipuncture after anesthetic induction, but prior to skin incision for appendectomy. All cases of appendicitis were confirmed by intraoperative findings and pathology of the removed appendix. Control Patients: Patients included in the control arm (n=9) were patients who were found not to have appendicitis, by both CT scanning and clinical follow-up. This included patients with reported abdominal pain, later found to be caused by diverticulitis, or other gastrointestinal pathologies, but not clinically associated with appendicitis. Blood was drawn at study enrollment for these patients.

Validation Set: Control Patients. Because appendicitis can involve infection, we enrolled 5 patients with lower respiratory tract infections (LRI) in the ED as an 'infection' control. Also, as a control for surgical factors, we enrolled 5 patients undergoing elective ventral hernia or inguinal hernia repair (HER), and these were compared with 10 new patients with surgically confirmed appendicitis (APP). In all surgical patients, including appendicitis and hernia repairs, research blood samples were drawn by venipuncture after anesthetic induction, and prior to skin incision. Two patients, (1 HER, 1 APP) were excluded due to technical complications in RNA purification or microarray analysis.

Blood Samples.

Blood was drawn in 3.2% sodium citrate tubes for frozen plasma samples, in Tempus Blood RNA tubes (ABI) for genome-wide RNA profiling, and in BD Vacutainer K2 tubes for complete blood counts with differentials.

RNA Purification for Transcript Profiling.

Tempus Blood RNA preservation tubes were stored at −80° C. and then thawed at 37° C. prior to processing according to manufacturer's methods. Total RNA was purified from whole blood using Tempus Blood RNA kit (ABI), followed by an aggressive DNAse treatment. Briefly, the preserved whole blood was pelleted at 3000×g for 30 minutes in a 4° C. refrigerated centrifuge, redissolved in lysis buffer and nucleic acids were bound to a column. After washing, nucleic acids were eluted with RNAse/DNAse free water and quantified by with NanoDrop ND-1000 spectrophotometer. DNA was eliminated by aggressive DNAse treatment (TurboDNAse, Ambion) at 2 U/10 µg nucleic acids, followed by affinity removal of the DNAse. The remaining RNA was quantified and RNA integrity was evaluated by 260/280 ratio on ND-1000 and by capillary electrophoresis on a Bioanalyzer 2100 (Agilent). RIN scores >7 were considered acceptable for further sample processing and did not differ between groups.

Microarray Expression Profiling and Analysis.

Purified RNA (100 ng) was labeled with the Illumina cRNA synthesis kit and hybridized to Illumina Human HT-12v4 Expression BeadChip arrays (http://www.illumina.com/products/humanht_12_expression_beadchip_kits_v4.html) containing more than 47,000 probes derived from the NCBI RefSeq release 38 (http://www.ncbi.nlm.nih.gov/refseq/). The arrays were washed and then fluorescence was quantitated on an Illumina HiScan (http://www.illumina.com/systems/hiscan.html).

The fluorescence levels per bead were converted to transcript levels using Illumina GeneStudio, which averaged typically 30 beads per transcript to produce a mean expression level for each of the 46K transcripts. Raw BeadChip fluorescence values were imported into GeneSpring GX12.5 with normalization to the 75-percentile of expression, but without baseline transformation. The main effect of identifying differentially expressed genes (DEG) with respect to appendicitis versus controls was achieved by a combined filter for a p value <0.05 on t test without correction for multiple testing, and 2) fold change >2.0. The DEG list was further analyzed for gene ontologies using DAVID [17]. Using the DEG list, a partial least squares discriminant (PLSD) prediction model was built in GeneSpring and internally validated with a Leave One Out Cross Validation (LOOCV) algorithm. The PLSD model was externally tested by applying the algorithm to a separate validation set of microarray samples not involved in building the model.

The PLSD model described here can be replicated by one of ordinary skill in the art by entering the PLSD loading weights for the genes disclosed in Tables 2 and 3 (below) into a suitable statistical package; in the instant invention, GeneSpring GX13 (Agilent) was used (http://www.genomics.agilent.com/en/product.jsp?cid=AG-PT-130&tabId=AG-PR-1061&_requestid=163669). Tables 5A and 5B below summarizes the loading weights for the genes of Table 2 and Table 3.

Results

Clinical Parameters.

As shown in Table 1, the clinical parameters between patients presenting with appendicitis versus other abdominal indications in the discovery set were generally similar. Age, gender, and body mass index (BMI) were comparable, although the appendicitis patients were principally of Caucasian race. Notably, white blood cell (WBC) counts were comparable, but appendicitis patients had 10% higher neutrophil count that was not statistically significant (77.18% vs 70%, NS). Appendicitis patients had significantly lower blood creatinine level (0.78 vs 1.54 mg/dL, p=0.03 uncorrected). The two groups did not yield significantly different RNA quantities from blood, and the amplification of RNA for microarray labeling was similar.

TABLE 1

Clinical Parameters of Discovery Set

|  |  |  | Appy (11) | ABD (9) |
|---|---|---|---|---|
| Gender |  | % male | 55.00 | 55 |
| Age | Mean | Years | 40.73 | 45.89 |
|  | SD |  | 15.45 | 15.54 |
| BMI | Mean |  | 24.51 | 26.44 |
|  | SD |  | 4.92 | 4.48 |
| Race |  | % White | 100.00 | 55.56 |
|  |  | % Black | 0.00 | 44.44 |
| Smoker |  | % | 18.18 | 11.11 |
| Duration of Symptom | Mean | Hours | 29.45 | 32.75 |
|  | SD |  | 18.68 | 30.65 |
| Temperature | Mean | Celsius | 36.97 | 36.8 |
|  | SD |  | 0.47 | 0.38 |
| WBC | Mean | K/ul | 13.06 | 13.23 |
|  | SD |  | 6.44 | 30.65 |
| Elevated Neutrophils | >75% | % | 55.00 | 37.5 |
| Neutrophils | Mean | % WBC | 77.18 | 70 |
|  | SD |  | 8.76 | 10.14 |
| Creatinine | Mean |  | 0.78 | 1.54 |
|  | SD |  | 0.13 | 1.06 |
| pH | <7.35 | % | 0.00 | 11.11 |
| Na < 130 |  | % | 0.00 | 0.00 |
| HCT < 30 |  | % | 0.00 | 11.11 |
| Glu > 250 |  | % | 0.00 | 0.00 |
| BUN > 30 |  | % | 0.00 | 0.00 |
| Immunosupressed |  | % | 0 | 0 |
| Steroids |  | % | 0 | 0 |
| Antibiotic use |  | % | 0 | 0 |
| Oral Rehydration | Mean | % | 35.60 | ND |
| Therapy | SD |  | 10.74 | ND |
| Cirrhosis |  | % | 0 | 0 |
| Cancer |  | % | 0 | 0 |
| Total RNA conc. | Mean | ng/ul | 102.36 | 66.48 |
|  | SD |  | 72.49 | 34.06 |
| Folds amp. | Mean | Fold | 67.96 | 64.13 |
|  | SD |  | 60.48 | 35.81 |
| Defensin Score | Mean | RNA level | 1.26 | 2.62* |
|  | SD |  | 0.92 | 1.46 |

*indicates p < 0.05 (uncorrected probability)
% indicates the percent of patients exhibiting that trait, unless otherwise indicated Identification of RNA Biomarkers for Appendicitis in Whole Blood.

A scatterplot of the expression patterns in the 2 groups (FIG. 1) suggested that there was excellent linearity of quantitation over roughly 7 log 2 orders of magnitude, with globins being the most highly and identically expressed transcripts between groups. By comparing the expression profiles of the two groups, and filtering for both a t-test probability <0.05 and a fold-change of >2.0, 37 transcripts were identified as significantly differentially expressed (Table 2, above). Hierarchical clustering of the 37 DEG was conducted to observe the pattern of covariance of the transcripts in these patients. A heatmap of the expression of these 37 transcripts across all 20 patients in the discovery set is shown in FIG. 2.

FIG. 1 shows a scatterplot of transcript levels in patients with appendicitis. In FIG. 1, whole blood RNA from patients with acute, surgically confirmed appendicitis (n=11) or abdominal pain (n=9) was profiled for the expression level of 45,966 transcripts on Illumina BeadChip Arrays (12v4). The expression level of each transcript was averaged within groups and plotted on a log 2 scale to reveal transcripts which differ between more than 2-fold between groups (outside parallel lines).

Figure 2:
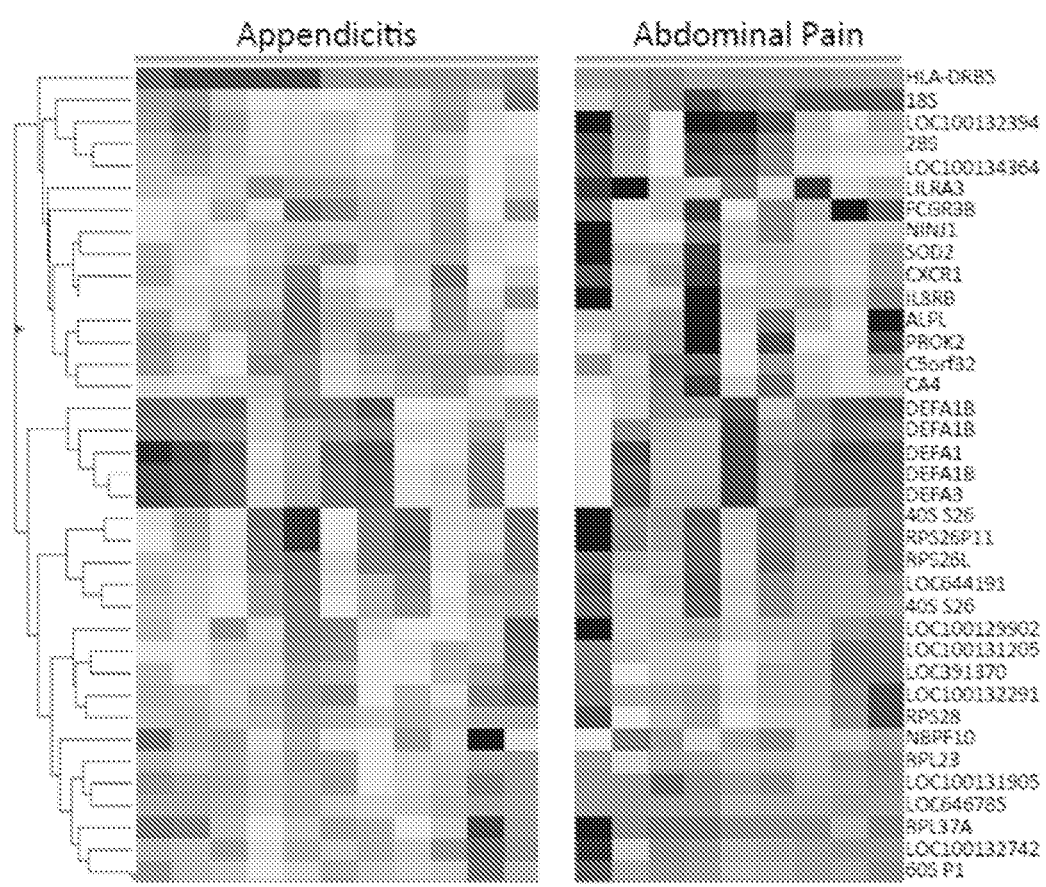
FIG. 2 shows hierarchical clustering of 37 differentially expressed genes in appendicitis patients.
Figure 6:
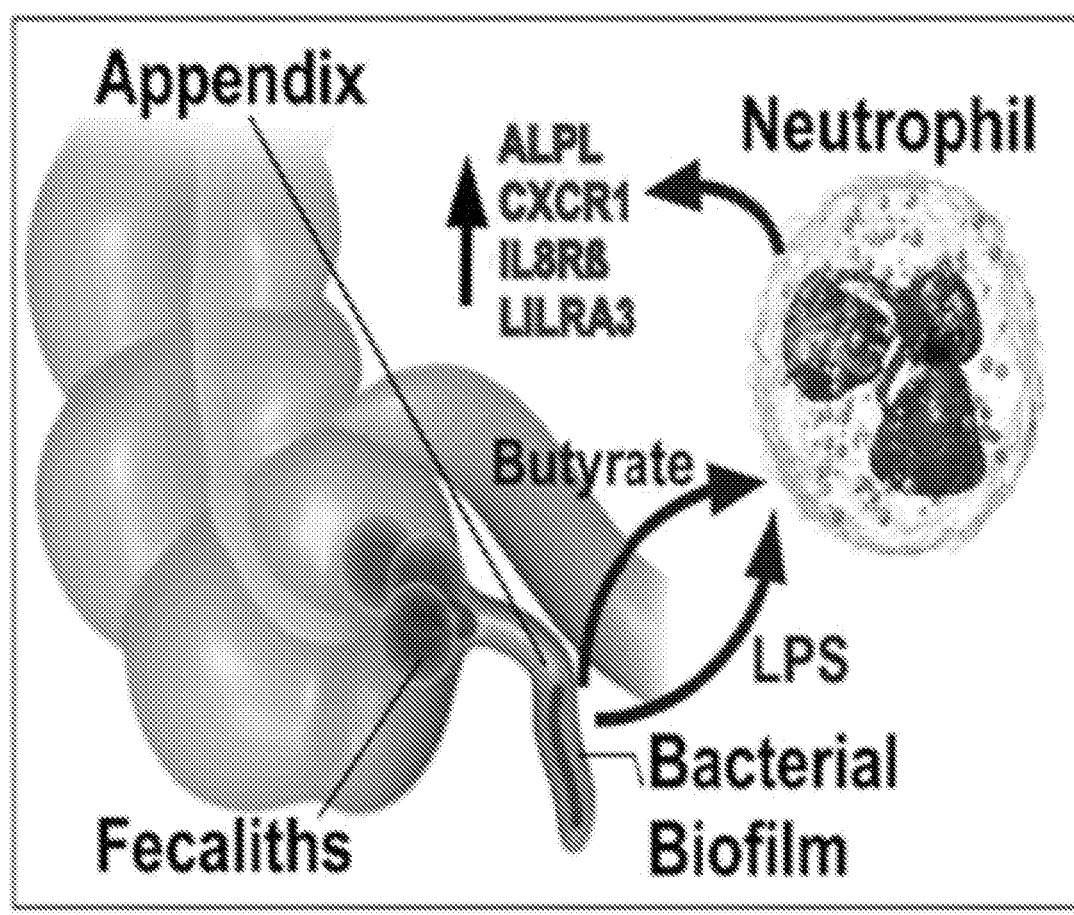
FIG. 6 shows a schematic of a model of appendicitis biomarker pathophysiology.

FIG. 2 shows hierarchical clustering of 37 differentially expressed genes in appendicitis patients. In FIG. 6, transcripts which differed between groups by >2-fold with a t-test probability of <0.05 (uncorrected) were identified by combined filtering. Following a per-gene normalization, DEGs were subjected to hierarchical clustering to identify patterns of covariance among the transcripts. The upper block of transcripts from HLA-DRB5 to CA4 are relatively higher in APP patients (red) compared to patients with other types of abdominal pain (yellow to blue). Conversely, transcripts from defensins (DEFA) and ribosomal transcripts, were relatively lower in APP than abdominal pain patients.

TABLE 2

Differentially expressed genes (DEG) sorted by functional grouping

| Probe ID | p Val | Fold Change | | Expression Level ABDOM | APPDX | DEFINITION | SYMBOL |
|---|---|---|---|---|---|---|---|
| CHEMOKINES and IMMUNE-RELATED | | | | | | | |
| 3440669 | 0.008 | 2.02 | ↑ | 1.85 | 2.86 | Chemokine C-X-C receptor 1 | CXCR1 |
| 2900327 | 0.003 | 2.59 | ↑ | 2.80 | 4.17 | Interleukin 8 receptor, β (CXCR2) | IL8RB |
| 1450139 | 0.004 | 3.07 | ↑ | 3.17 | 4.79 | Fc frag of IgG receptor IIIb (CD16b) | FCGR3B |
| 6370315 | 0.017 | 3.16 | ↑ | −0.11 | 1.55 | MHC class II, DR beta 5 | HLA-DRB5 |
| 6110037 | 0.007 | 2.36 | ↑ | 2.38 | 3.62 | Leukocyte IgG-like receptor A3 | LILRA3 |
| DEFENSINS | | | | | | | |
| 4540239 | 0.019 | 2.80 | ↓ | 3.39 | 1.91 | Defensin, alpha 1 | DEFA1 |
| 870477 | 0.024 | 2.29 | ↓ | 2.60 | 1.40 | Defensin, alpha 1B (3 probesets) | DEFA1B |
| 2970747 | 0.017 | 2.69 | ↓ | 2.58 | 1.15 | Defensin, alpha 3, neutrophil-spec. | DEFA3 |
| TRANSLATION and PROTEIN SYNTHESIS | | | | | | | |
| 3180609 | 0.002 | 2.69 | ↑ | 1.04 | 2.47 | 18S ribosomal RNA, non-coding | 18S rRNA |
| 6280504 | 0.005 | 2.05 | ↑ | 1.20 | 2.23 | 28S ribosomal RNA, non-coding | 28S rRNA |
| 3190348 | 0.007 | 2.01 | ↓ | 2.16 | 1.15 | 60S acidic ribosomal protein P1 | RPLP1 |
| 6270307 | 0.006 | 2.04 | ↓ | 2.04 | 1.01 | 40S ribosomal protein S26 (3 sets) | RPS26 |
| 380575 | 0.000 | 2.14 | ↓ | 1.49 | 0.39 | Ribosomal protein L23 | RPL23 |
| 990273 | 0.012 | 2.48 | ↓ | 3.39 | 2.08 | Ribosomal protein L37a | RPL37A |
| 650349 | 0.008 | 2.00 | ↓ | 2.20 | 1.19 | Ribosomal protein S28 | RPS28 |
| STRESS and INJURY RELATED | | | | | | | |
| 6100356 | 0.002 | 2.84 | ↑ | 3.63 | 5.14 | Alkaline phosphatase, liver/bone | ALPL |
| 6380672 | 0.001 | 2.11 | ↑ | 1.42 | 2.50 | Carbonic anhydrase IV | CA4 |
| 1510681 | 0.012 | 2.01 | ↓ | 3.56 | 2.55 | Neuroblastoma breakpt family 10 | NBPF10 |
| 7380706 | 0.001 | 2.10 | ↑ | 2.61 | 3.68 | Ninjurin 1 | NINJ1 |
| 1030463 | 0.004 | 2.49 | ↑ | 3.30 | 4.62 | Prokineticin 2 | PROK2 |
| 3890326 | 0.011 | 2.02 | ↑ | 3.43 | 4.44 | Superoxide dismutase 2, mitochon. | SOD2 |
| MINIMALLY ANNOTATED | | | | | | | FROM NCBI |
| 6420563 | 0.023 | 2.00 | ↓ | 3.85 | 2.85 | LOC100129902 | RPS29P11 |
| 650735 | 0.001 | 2.09 | ↓ | 1.86 | 0.79 | LOC100131205 | RPL21P28 |
| 6650603 | 0.000 | 2.66 | ↓ | 1.95 | 0.54 | LOC100131905 | RPS27P21 |
| 7150414 | 0.003 | 2.31 | ↓ | 2.26 | 1.06 | LOC100132291 | RPS27P29 |
| 4670634 | 0.003 | 2.81 | ↑ | 1.69 | 3.18 | LOC100132394 | retired |
| 6580017 | 0.009 | 2.18 | ↓ | 2.81 | 1.69 | LOC100132742 | RPL17L |
| 2630347 | 0.001 | 2.04 | ↑ | 1.17 | 2.21 | LOC100134364 | retired |
| 3390674 | 0.002 | 2.01 | ↓ | 2.11 | 1.10 | LOC391370 | RPS12P4 |
| 1170551 | 0.001 | 2.19 | ↓ | 1.55 | 0.42 | LOC646785 | RPS10P13 |
| 6960373 | 0.013 | 2.00 | ↓ | 2.23 | 1.23 | LOC644191 | RPS26P8 |
| 4540241 | 0.005 | 2.15 | ↑ | 1.10 | 2.21 | C5orf32 | CYSTM1 |

TABLE 3

A sixteen transcript set predictive of appendicitis

| PROBE_ID | SYMBOL | ProbeID | p | FC (abs) | Change | ABDOM expression level | APP expression level |
|---|---|---|---|---|---|---|---|
| ILMN_1701603 | ALPL | 6100356 | 0.001874699 | 2.84 | up | 3.63 | 5.14 |
| ILMN_1761566 | C5orf32 | 4540241 | 0.004890986 | 2.15 | up | 1.10 | 2.21 |
| ILMN_1697499 | HLA-DRB5 | 6370315 | 0.017076675 | 3.16 | up | −0.11 | 1.55 |
| ILMN_1680397 | IL8RB | 2900327 | 0.002848122 | 2.59 | up | 2.8 | 4.17 |
| ILMN_1661631 | LILRA3 | 6110037 | 0.007226919 | 2.36 | up | 2.38 | 3.62 |
| ILMN_3243593 | LOC100008588 | 3180609 | 0.001715004 | 2.69 | up | 1.04 | 2.47 |
| ILMN_1733559 | LOC100008589 | 6280504 | 0.005007231 | 2.05 | up | 1.2 | 2.23 |
| ILMN_3249578 | LOC100132394 | 4670634 | 0.003334389 | 2.81 | up | 1.69 | 3.18 |
| ILMN_3246805 | LOC100134364 | 2630347 | 8.80E-04 | 2.04 | up | 1.17 | 2.21 |
| ILMN_3293367 | LOC391370 | 3390674 | 0.001937386 | 2.01 | down | 2.11 | 1.1 |
| ILMN_3209193 | LOC644191 | 6960373 | 0.012769181 | 2.00 | down | 2.23 | 1.23 |
| ILMN_2155719 | NBPF10 | 1510681 | 0.012251468 | 2.01 | down | 3.56 | 2.55 |
| ILMN_1815086 | NINJ1 | 7380706 | 7.91E-04 | 2.10 | up | 2.61 | 3.68 |
| ILMN_1775257 | PROK2 | 1030463 | 0.004478186 | 2.49 | up | 3.3 | 4.62 |
| ILMN_1755115 | RPL23 | 380575 | 9.09E-05 | 2.14 | down | 1.49 | 0.39 |
| ILMN_2336781 | SOD2 | 3890326 | 0.010532255 | 2.02 | up | 3.43 | 4.44 |

Certain aspects of this expression pattern increase the confidence that some of these changes are non-random: 1) multiple probe sets identifying the same transcript (DEFA1), 2) 'hits' on highly related transcripts such as DEFA1 and DEFA3, as well as CXCR1 (aka IL8 receptor α) and IL8 receptor β.

TABLE 4

DEG gene symbols and Genbank IDs

| Probe ID | Gene Symbol | Definition | Genbank ID(s) |
|---|---|---|---|
| 6100356 | ALPL | *Homo sapiens* alkaline phosphatase, liver/bone/kidney (ALPL), transcript variant 1, mRNA. | AL592309 AB011406<br>BC066116 AB012643<br>BC136325 NM_000478<br>NM_001127501<br>AL359815 X53750<br>BC021289 AB209814<br>D87880 D87882<br>D87881 AK298085<br>M24429 BC126165<br>M24428 BC110909<br>D87877 D87887<br>D87876 CH471134<br>D87888 D87879<br>D87889 D87878<br>D87883 AK312667<br>D87884 DA625627<br>D87875 D87885<br>D87874 D87886<br>DA631560 M24435<br>M24434 M24433<br>M24432 BC090861<br>M24431 M24430<br>AK293184 M24439<br>M24438 M24437<br>M24436 AK295608<br>X14174 AK097413 |
| 4540241 | C5orf32 | *Homo sapiens* chromosome 5 open reading frame 32 (C5orf32), mRNA. | BC023982 AJ245877<br>CH471062 BM919999<br>AC011379 CR607630<br>AK225992 BC013643<br>AK312045 CA310907<br>CR615127 CR603819<br>AC011380 NM_032412 |
| 6380672 | CA4 | *Homo sapiens* carbonic anhydrase IV (CA4), mRNA. | AK298710 AC025048<br>NM_000717 M83670<br>AK289715 BC069649<br>DA113846 L10953<br>L10954 L10955<br>L10951 AI990988<br>BC074768 CH471109<br>BC057792 CR541766 |

TABLE 4-continued

DEG gene symbols and Genbank IDs

| Probe ID | Gene Symbol | Definition | Genbank ID(s) |
|---|---|---|---|
| 3440669 | CXCR1 | *Homo sapiens* chemokine (C-X-C motif) receptor 1 (CXCR1), mRNA. | CR542029 AY916763 AY916764 AY916762 CR541994 BC072397 DQ894895 L19591 L19592 AB032732 AY651785 M68932 U11871 AY916766 U11870 CR617846 AY916765 BC028221 X65858 AK312668 AB032730 AB032731 AY916769 CH471063 NM_000634 AY916772 AY916773 AC097483 AK298647 AB032729 AB032728 AK309632 CA425329 DQ891718 |
| 4540239 | DEFA1 | *Homo sapiens* defensin, alpha 1 (DEFA1), mRNA. | AX405718 L12690 NM_004084 AF238378 AF200455 BC069423 X52053 AF233439 M26602 BC093791 DQ896798 DQ890546 DQ890545 NM_001042500 BC112188 M21130 |
| 870477 | DEFA1B | *Homo sapiens* defensin, alpha 1B (DEFA1B), mRNA. | AX405718 L12690 NM_004084 AF238378 AF200455 BC069423 X52053 AF233439 M26602 BC093791 DQ896798 DQ890546 DQ890545 NM_001042500 BC112188 M21130 |
| 4860128 | DEFA1B | *Homo sapiens* defensin, alpha 1B (DEFA1B), mRNA. | AX405718 L12690 NM_004084 AF238378 AF200455 BC069423 X52053 AF233439 M26602 BC093791 DQ896798 DQ890546 DQ890545 NM_001042500 BC112188 M21130 |
| 7150170 | DEFA1B | *Homo sapiens* defensin, alpha 1B (DEFA1B), mRNA. | AX405718 L12690 NM_004084 AF238378 AF200455 BC069423 X52053 AF233439 M26602 BC093791 DQ896798 DQ890546 DQ890545 NM_001042500 BC112188 M21130 |
| 2970747 | DEFA3 | *Homo sapiens* defensin, alpha 3, neutrophil-specific (DEFA3), mRNA. | L12691 EU176174 M23281 X13621 NM_005217 AF238378 BC027917 AF200455 M21131 BC119706 |
| 1450139 | FCGR3B | *Homo sapiens* Fc fragment of IgG, low affinity IIIb, receptor (CD16b) (FCGR3B), mRNA. | AK316565 M24854 AL451067 BC128562 NM_000570 X07934 AB032414 Z46223 AK313219 X16863 DA672763 AJ581669 J04162 AB025256 |
| 6370315 | HLA-DRB5 | *Homo sapiens* major histocompatibility complex, class II, DR beta 5 (HLA-DRB5), mRNA. | AF112878 Y17695 AF112877 X65585 AF243537 AY050211 AF029286 U68391 AF029285 AY465115 AF029282 AY050208 AF029283 AY050207 M98436 M16955 AF327742 M16954 AF029281 M16956 AY663412 DQ835614 AY770514 M63216 AF011786 AY267905 AF029267 AJ251984 M77671 AY396024 |

TABLE 4-continued

DEG gene symbols and Genbank IDs

| Probe ID | Gene Symbol | Definition | Genbank ID(s) |
|---|---|---|---|
| | | | AY267906 AF029273 |
| | | | AF029274 AF029275 |
| | | | DQ837166 AJ783982 |
| | | | AY050214 AF029270 |
| | | | AB112913 AF029271 |
| | | | AB112912 AF029272 |
| | | | AY770520 AJ242985 |
| | | | AY663404 U79027 |
| | | | U79025 U79026 |
| | | | AF288212 X99841 |
| | | | U59685 AL713966 |
| | | | M91001 D13412 |
| | | | AY641577 X64544 |
| | | | AJ566209 AF335232 |
| | | | U34602 X64548 |
| | | | Y13727 X64549 |
| | | | AF029291 AJ252281 |
| | | | AY141137 EF078986 |
| | | | AY052549 AY884215 |
| | | | AJ506752 AM231063 |
| | | | AJ534885 AJ512947 |
| | | | M74032 M16086 |
| | | | X87210 M63197 |
| | | | M20429 AJ427352 |
| | | | AY247411 AY502108 |
| | | | M15839 Y17819 |
| | | | AF335230 L26306 |
| | | | X99895 U25638 |
| | | | AF047350 M57600 |
| | | | AY172512 DQ987876 |
| | | | AY179368 AY179367 |
| | | | AY179366 AJ491301 |
| | | | AJ867236 U95818 |
| | | | U41634 M14661 |
| | | | AJ506201 AF034858 |
| | | | EF419344 D14352 |
| | | | AF406781 D88310 |
| | | | U72264 AJ878425 |
| | | | AJ249726 DQ514604 |
| | | | DQ525634 AJ854064 |
| | | | U66721 AY899913 |
| | | | AJ245714 AJ245715 |
| | | | AJ245717 AM000036 |
| | | | X95656 U66826 |
| | | | AJ243897 AY277387 |
| | | | AJ243898 AJ580838 |
| | | | M27689 AJ311892 |
| | | | AF247534 AF247533 |
| | | | U37583 AY259126 |
| | | | AY277393 AY277390 |
| | | | AY277391 AK314834 |
| | | | AY259128 U72064 |
| | | | Z83201 X97291 |
| | | | DQ179043 AY054375 |
| | | | DQ179042 U41489 |
| | | | AY504812 M81174 |
| | | | AY504813 AF329281 |
| | | | AJ297705 AF306862 |
| | | | AJ238410 AJ539471 |
| | | | M81171 Y09342 |
| | | | AY307897 D89917 |
| | | | U08275 U08274 |
| | | | M30182 M30181 |
| | | | AY663397 U95115 |
| | | | AB010270 AM159646 |
| | | | AF164346 DQ535034 |
| | | | AB010269 AY257483 |
| | | | AY429728 AJ515905 |
| | | | AY429723 M81180 |
| | | | AY877348 X73027 |
| | | | M57648 AF093411 |
| | | | DQ135944 AJ507780 |
| | | | AF089719 AJ297582 |
| | | | D49468 AY174184 |
| | | | AY174181 AB049832 |
| | | | AY050186 AF339884 |

TABLE 4-continued

DEG gene symbols and Genbank IDs

| Probe ID | Gene Symbol | Definition | Genbank ID(s) |
|---|---|---|---|
| | | | AB062112 DQ140279 AJ404618 M20503 AJ854250 AF169239 NM_002125 U96926 M17377 AF052574 DQ179034 AF267639 M17379 AF142465 M17384 AJ507382 M59798 M17387 AF142466 AF029301 M17383 M17382 M32578 AY296120 AY296121 AY170862 AJ271159 EF495154 U26558 Y07590 AF142451 AJ871009 S79786 AJ441130 AB106129 AF122887 AF201762 X96396 U17381 AJ289124 AJ306404 AY545466 DQ643390 DQ060439 D29836 AJ507425 AF186408 AF442519 AB087875 AB176444 AF186407 Z99006 U25442 AY048687 M15992 CH878642 AF142447 AY305859 AF142442 AY664400 AF142445 AY664401 AF450093 AF234175 X86803 AF490771 U31770 AF004817 AJ401148 BC009234 AF234181 AJ488066 AJ243327 FN430425 AF144080 AM084908 AY379480 M35159 L21755 AY331806 AF081676 AY457037 AK292140 AY765349 L41992 |
| 2900327 | IL8RB | Homo sapiens interleukin 8 receptor, beta (IL8RB), mRNA. | U11869 DA670033 U11866 AK290906 DQ895671 NM_001168298 DA674925 L19593 AB032733 AC124768 AB032734 U11873 U11872 DQ893661 AK312664 M73969 U11874 U11875 AY714242 AJ710879 U11876 U11877 CH471063 U11878 M94582 BC037961 M99412 NM_001557 |
| 6110037 | LILRA3 | Homo sapiens leukocyte immunoglobulin-like receptor, subfamily A (without TM domain), member 3 (LILRA3), mRNA. | AF482762 AF482763 U91926 U91927 AF482766 AF482767 BC028208 AF482764 AF482765 NM_006865 AF025527 DQ894258 AF014923 AF014924 AF353733 AC010518 DQ891075 CH471135 AF482769 AF482768 |
| 3180609 | LOC100008588 | Homo sapiens 18S ribosomal RNA (LOC100008588), non-coding RNA. | NT_167214.1 |

TABLE 4-continued

DEG gene symbols and Genbank IDs

| Probe ID | Gene Symbol | Definition | Genbank ID(s) |
| --- | --- | --- | --- |
| 6280504 | LOC100008589 | *Homo sapiens* 28S ribosomal RNA (LOC100008589), non-coding RNA. | AK225361 NM_033331 EF611343 NM_003671 AF023158 AF064104 AL133477 NM_001077181 AF064105 AL353578 AY675321 AK126388 CR601692 BC156666 BC050013 DA943563 CH471174 U13369 NR_003287 AL592188 |
| 6280504 | LOC100008589 | *Homo sapiens* 28S ribosomal RNA (LOC100008589), non-coding RNA. | NT_167214.1 |
| 6420563 | LOC100129902 | PREDICTED: *Homo sapiens* similar to mCG7602 (LOC100129902), mRNA. | NC_000004.10 |
| 650735 | LOC100131205 | PREDICTED: *Homo sapiens* hypothetical protein LOC100131205, transcript variant 3 (LOC100131205), mRNA. | NR_026911 |
| 6650603 | LOC100131905 | PREDICTED: *Homo sapiens* misc_RNA (LOC100131905), miscRNA. | NC_000012.10 |
| 7150414 | LOC100132291 | PREDICTED: *Homo sapiens* similar to hCG2027326 (LOC100132291), mRNA. | NC_000019.8 |
| 4670634 | LOC100132394 | PREDICTED: *Homo sapiens* hypothetical protein LOC100132394 (LOC100132394), mRNA. | n/a |
| 6580017 | LOC100132742 | PREDICTED: *Homo sapiens* hypothetical protein LOC100132742, transcript variant 1 (LOC100132742), mRNA. | NC_000001.9 |
| 2630347 | LOC100134364 | PREDICTED: *Homo sapiens* hypothetical protein LOC100134364 (LOC100134364), mRNA. | n/a |
| 3390674 | LOC391370 | PREDICTED: *Homo sapiens* similar to hCG1818387 (LOC391370), mRNA. | NC_000002.10 |
| 3190348 | LOC440927 | PREDICTED: *Homo sapiens* similar to 60S acidic ribosomal protein P1, transcript variant 4 (LOC440927), mRNA. | n/a |
| 6960373 | LOC644191 | PREDICTED: *Homo sapiens* similar to hCG15685, transcript variant 1 (LOC644191), mRNA. | NC_000017.9 |
| 6270307 | LOC644934 | PREDICTED: *Homo sapiens* similar to 40S ribosomal protein S26, transcript variant 1 (LOC644934), mRNA. | AL353735 AC225613 AC090543 AC034102 CH471054 DQ896038 CH471057 AL136526 BC105798 AC098847 AB007161 AC006463 U41448 AC008065 AB007160 X69654 AP004217 DQ895081 X79236 AL138767 AV681946 AC126544 CH236947 DQ891895 BC013215 BC070220 BC105276 DQ896089 AC012391 DQ892791 AC027373 NM_001029 AC004057 X77770 AC025518 BC015832 CR611958 BC002604 |
| 1170551 | LOC646785 | PREDICTED: *Homo sapiens* misc_RNA (LOC646785), miscRNA. | NC_000006.10 |

TABLE 4-continued

DEG gene symbols and Genbank IDs

| Probe ID | Gene Symbol | Definition | Genbank ID(s) |
| --- | --- | --- | --- |
| 6960195 | LOC650646 | PREDICTED: *Homo sapiens* similar to 40S ribosomal protein S26 (LOC650646), mRNA. | AL445193 CH471059 |
| 1510681 | NBPF10 | *Homo sapiens* neuroblastoma breakpoint family, member 10 (NBPF10), mRNA. XM_930727 XM_930739 XM_930751 XM_930759 XM_930766 XM_930776 XM_930785 XM_930797 XM_930808 XM_930830 XM_930841 XM_930850 XM_930862 XM_930872 XM_930880 XM_930889 XM_930897 XM_930903 XM_930910 XM_930917 XM_930926 XM_930936 XM_930943 XM_930951 XM_930954 XM_930961 XM_930967 XM_930975 XM_930985 XM_930993 XM_931003 XM_931009 XM_931015 XM_931021 XM_931027 XM_931033 XM_931038 XM_931044 XM_931049 XM_931055 XM_931060 XM_931066 XM_931069 XM_931072 XM_931076 XM_931080 XM_931084 XM_931090 XM_931096 XM_931102 XM_931110 XM_931119 XM_931125 XM_931131 XM_931137 XM_931138 XM_931145 XM_931149 XM_931157 XM_931161 XM_931164 XM_931169 XM_931174 XM_931178 XM_931183 XM_931188 XM_931191 XM_931196 XM_931202 XM_931208 XM_931213 XM_931221 XM_931229 XM_931234 XM_931240 XM_931245 XM_931251 XM_931255 XM_931259 XM_931264 XM_931269 XM_931277 XM_931282 XM_931291 XM_931299 XM_931308 XM_931317 XM_931322 XM_931328 XM_931335 | NM_001101663 BC094705 AK055895 AL049742 AF379606 AK095030 AF379607 BC034418 CR599564 XM_002346226 CR608846 BC169317 BC169318 BC169316 BC094841 DB300232 AF380582 NM_001037675 BC086308 AL117237 AF380580 NM_183372 BC063799 BX546486 BC027348 AL592284 NM_001039703 AC026900 AK302413 AF379624 NM_015383 AF379626 AF379627 AF379628 AK294944 XM_001726946 AK092351 AF379620 AF379621 AF379622 AF379623 AK054850 AL359176 XM_001717398 AF379615 AF379616 AF379613 AF131738 AF379614 AL355149 AF379619 AL138796 BX511041 AK290302 AF379617 AL050141 AF379618 BC021111 AF379611 AF379612 AY894574 BC010124 AY894573 BC148331 AY894572 AL040349 AY894571 AY894570 BC071995 AY894579 AY894578 AY894577 AL592307 AY894576 AY894575 AL137798 AK290142 AI865471 AF419617 XM_001715810 AF419616 AF419619 AF419618 AK095459 AF379632 AY894583 AF379631 AL356004 AY894582 AF379634 AY894585 BC110431 AF379630 AY894581 AK125792 AY894580 AL139152 BC167783 AK294414 AF379635 NM_017940 AF420437 BQ890458 AK000726 BC136292 CR600619 AL954711 BC071723 AF161426 BI552657 AB051480 CR610345 AK097180 BC023087 BX648497 AL022240 AL832622 AB033071 AY894561 BC013805 AY894563 AY894562 BC066930 AY894565 AY894567 AY894566 BX538005 AY894569 AY894568 BX842679 NM_173638 DQ786323 AK299360 NM_001170755 BC093404 AK123260 |
| 7380706 | NINJ1 | *Homo sapiens* ninjurin 1 (NINJ1), mRNA. | AL451065 BC048212 AK094530 BT007164 U91512 BC019336 AF029251 CH471089 |

TABLE 4-continued

DEG gene symbols and Genbank IDs

| Probe ID | Gene Symbol | Definition | Genbank ID(s) |
|---|---|---|---|
| 1030463 | PROK2 | *Homo sapiens* prokineticin 2 (PROK2), mRNA. | U72661 BC004440 CR608271 CR595190 NM_004148 BC000298 AC096970 AY349131 CS023558 BC098110 CH471055 NM_021935 BC069395 AF333025 NM_001126128 BC098162 BC096695 AF182069 |
| 380575 | RPL23 | *Homo sapiens* ribosomal protein L23 (RPL23), mRNA. | X52839 AC110749 BC034378 BC106061 CR604268 X55954 CR610098 BC104651 CH471152 NM_000978 AB061827 AL136089 BC003518 DQ893218 CA437923 BC062716 DQ896547 BC010114 AK024749 |
| 990273 | RPL37A | *Homo sapiens* ribosomal protein L37a (RPL37A), mRNA. | CR618026 CR542152 BC016748 L22154 CH471063 BC047872 CR613913 BC039030 BC014262 BC067789 NM_000998 L06499 CD249666 AC073321 BC063476 X66699 BC082239 AK291857 BC000555 AK289472 D28355 |
| 5890730 | RPS26L | PREDICTED: *Homo sapiens* 40S ribosomal protein S26-like (RPS26L), misc RNA. | AL136526 |
| 6560376 | RPS26P11 | *Homo sapiens* ribosomal protein S26 pseudogene 11 (RPS26P11), non-coding RNA. | NR_002309 AL929401 AW972305 |
| 650349 | RPS28 | *Homo sapiens* ribosomal protein S28 (RPS28), mRNA. | AB007164 CH471076 AU126783 BC021239 AC107983 L05091 AC005011 CR606185 DQ891357 U58682 CR603137 AK293636 BC070217 BC070218 CH471139 AC010323 AK301638 BC018810 DQ894538 CR457055 CH236952 NM_001031 AB061846 BC000354 AK311925 |
| 3890326 | SOD2 | *Homo sapiens* superoxide dismutase 2, mitochondrial (SOD2), nuclear gene encoding mitochondrial protein, transcript variant 2, mRNA. | X65965 BC035422 CH471051 BU164685 DQ003134 DQ890587 Y00472 X59445 AK097395 AM392836 AY280721 AK304766 AY280720 AY267901 BT006967 BU741675 AY280719 AY280718 Y00985 NM_001024465 NM_001024466 BC016934 CR626136 AK296809 S77127 L34157 X14322 BC001980 NM_000636 D83493 M36693 AL691784 X07834 AK313082 X15132 AL050388 AL135914 DQ893752 BC012423 BG699596 BM994509 |

TABLE 5A

PLSD loading weights for genes from Table 2:

| PROBE_ID | SYMBOL | PLSD Loading weight for Abdominal discomfort | PLSD Loading weight for Appendicitis |
|---|---|---|---|
| ILMN_1701603 | ALPL | 0.29783 | −0.29783 |
| ILMN_1761566 | C5orf32 | −0.25526 | 0.25526 |
| ILMN_1695157 | CA4 | −0.01612 | 0.01612 |
| ILMN_1662524 | CXCR1 | −0.06819 | 0.06819 |
| ILMN_2193213 | DEFA1 | −0.06522 | 0.06522 |
| ILMN_1679357 | DEFA1B | 0.04740 | −0.04740 |
| ILMN_1725661 | DEFA1B | −0.01104 | 0.01104 |
| ILMN_2102721 | DEFA1B | 0.03026 | −0.03026 |
| ILMN_2165289 | DEFA3 | −0.04788 | 0.04788 |
| ILMN_1728639 | FCGR3B | 0.04584 | −0.04584 |
| ILMN_1697499 | HLA-DRB5 | −0.33313 | 0.33313 |
| ILMN_1680397 | IL8RB | −0.16264 | 0.16264 |
| ILMN_1661631 | LILRA3 | −1.50443 | 1.50443 |
| ILMN_3243593 | LOC100008588 | 0.33584 | −0.33584 |
| ILMN_1733559 | LOC100008589 | −0.27838 | 0.27838 |
| ILMN_3256742 | LOC100129902 | 0.17543 | −0.17543 |
| ILMN_3214532 | LOC100131205 | 0.57084 | −0.57084 |
| ILMN_3275489 | LOC100131905 | 0.42307 | −0.42307 |
| ILMN_3275345 | LOC100132291 | 0.01674 | −0.01674 |
| ILMN_3249578 | LOC100132394 | −0.38482 | 0.38482 |
| ILMN_3202734 | LOC100132742 | 0.14064 | −0.14064 |
| ILMN_3246805 | LOC100134364 | −0.24811 | 0.24811 |
| ILMN_3293367 | LOC391370 | 0.21413 | −0.21413 |
| ILMN_1689712 | LOC440927 | 0.10489 | −0.10489 |
| ILMN_3209193 | LOC644191 | −0.25270 | 0.25270 |
| ILMN_1678522 | LOC644934 | −0.09154 | 0.09154 |
| ILMN_3210538 | LOC646785 | 0.01680 | −0.01680 |
| ILMN_1726647 | LOC650646 | −0.10099 | 0.10099 |
| ILMN_2155719 | NBPF10 | 0.51417 | −0.51417 |
| ILMN_1815086 | NINJ1 | −0.62920 | 0.62920 |
| ILMN_1775257 | PROK2 | 0.31264 | −0.31265 |
| ILMN_1755115 | RPL23 | 0.42432 | −0.42433 |
| ILMN_2051519 | RPL37A | 0.04629 | −0.04629 |
| ILMN_1750636 | RPS26L | 0.17768 | −0.17768 |
| ILMN_2180866 | RPS26P11 | −0.00077 | 0.00077 |
| ILMN_1651228 | RPS28 | 0.03448 | −0.03448 |
| ILMN_2336781 | SOD2 | −0.28727 | 0.28727 |

TABLE 5B

PLSD loading weights for genes from Table 3:

| PROBE_ID | SYMBOL | PLSD Loading weight for Abdominal discomfort | PLSD Loading weight for Appendicitis |
|---|---|---|---|
| ILMN_1701603 | ALPL | 0.30 | −0.30 |
| ILMN_1761566 | C5orf32 | −0.26 | 0.26 |
| ILMN_1697499 | HLA-DRB5 | −0.33 | 0.33 |
| ILMN_1680397 | IL8RB | −0.16 | 0.16 |
| ILMN_1661631 | LILRA3 | −1.50 | 1.50 |
| ILMN_3243593 | LOC100008588 | 0.34 | −0.34 |
| ILMN_1733559 | LOC100008589 | −0.28 | 0.28 |
| ILMN_3249578 | LOC100132394 | −0.38 | 0.38 |
| ILMN_3246805 | LOC100134364 | −0.25 | 0.25 |
| ILMN_3293367 | LOC391370 | 0.21 | −0.21 |
| ILMN_3209193 | LOC644191 | −0.25 | 0.25 |
| ILMN_2155719 | NBPF10 | 0.51 | −0.51 |
| ILMN_1815086 | NINJ1 | −0.63 | 0.63 |
| ILMN_1775257 | PROK2 | 0.31 | −0.31 |
| ILMN_1755115 | RPL23 | 0.42 | −0.42 |
| ILMN_2336781 | SOD2 | −0.29 | 0.29 |

Functional Analysis of DEG Transcripts.

Of the well annotated transcripts, several had prior published relationships to infection, immunity, or inflammation, or stress/injury: notably, alkaline phosphatase liver/bone/kidney isoform (ALPL), carbonic anhydrase IV (CA4), chemokine (C-X-C motif) receptor 1 (CXCR1), defensin a1 (DEFA1), defensin α3 (DEFA3), IgG Fc receptor Iib (FCGR3B/CD16B), interleukin 8 receptor ß (IL8RB), ninjurin 1, (NINJ1), prokinectin 2 (PROK2), and superoxide dismutase 2 (SOD2). In addition to their logical connection to appendicitis, which often has an infectious etiology, certain aspects of this expression pattern increase the confidence that some of these changes are non-random: 1) multiple probe sets identifying the same transcript (DEFA1), 2) 'hits' on highly related transcripts, such as DEFA1 and DEFA3, as well as CXCR1 (aka IL8 receptor ß) and IL8 receptor ß.

Defensins.

To understand the defensin pathway, the 5 α-defensin transcripts in the DEG list, which are all variant transcripts from the DEFA locus at 8p21.3, were averaged to create a 'defensin score', and then compared between groups (Table 1). Using a threshold determined by the mean of all 20 patients (1.87), 6 of 9 (67%) patients with other abdominal disorders showed elevated defensins, while only 1 of 11 (9%) of appendicitis patients had elevated defensin mRNA (see defensin cluster in FIG. 2). Surprisingly, the defensin score was essentially uncorrelated with white blood cell count (WBC) (r=0.07) and neutrophil % (r=0.15).

Other Immune/Inflammatory Pathways.

Interestingly, 3 of the 37 DEG (LILRA3, CXCR1/IL8RA, FCGR3A), which were higher in appendicitis patients compared to abdominal pain patients, are near or exact matches to transcripts discovered previously as down-regulated by exposure of isolated human neutrophils to E. Coli [18]. However, across the 20 patients, they were not inversely correlated with defensin expression (LILRA=0.02, CXCR1=−0.02, FCGR3A=−0.33), suggesting they are regulated independently of infectious markers. Other transcripts were readily associated with tissue injury or inflammation, but not previously associated with pathogen infection. For instance, NINJ1 was identified as a transcript strongly upregulated after peripheral nerve injury [19]. PROK2 is elevated in colitis tissue [20], which, like appendicitis, is an inflammatory condition in the GI tract. Likewise, ALPL has a well-known role in modulating diverse inflammatory conditions not limited to infectious disease [21].

Ribosomal Transcripts.

While it is widely assumed that ribosomal RNAs (rRNA), such as 18S and 28S non-coding RNAs are 'invariant', or 'housekeeping' transcripts, there is considerable evidence that they are carefully regulated in cases such as granulocyte activation [22], and differ significantly in prostate cancer [23], and in hepatitis C infected livers [24]. In fact, early studies with PHA-activated human lymphocytes demonstrated as much as 8-fold increases in rRNA levels within 20 hours [25,26]. Furthermore, if the observed changes were due to some type of loading or processing anomaly, then we would expect all of the ribosomal RNAs to be affected in the same direction, when in fact, 18S and 28S noncoding transcripts were increased in appendicitis, but most of the transcripts coding for ribosomal proteins were decreased, suggesting that this is a regulated process.

Minimally Annotated Transcripts.

Of the 37 DEG, 11 transcripts were minimally annotated, i.e. 'predicted transcript', but further manual annotation using NCBI Gene revealed high likelihood assignments. Remarkably, 8 of the 11 transcripts were identified as ribosomal protein pseudogenes, which is quite unlikely to have occurred by chance. Two transcripts have been discontinued, and the eleventh was identified as CYSTM1 (C50RF32), which is a cysteine-rich transmembrane module-containing protein that 2-hybrid screens identified as an inhibitor of the glucagon-like peptide 1 receptor (GLP-1R) [27].

Prediction of Appendicitis from DEG.

Figure 3:
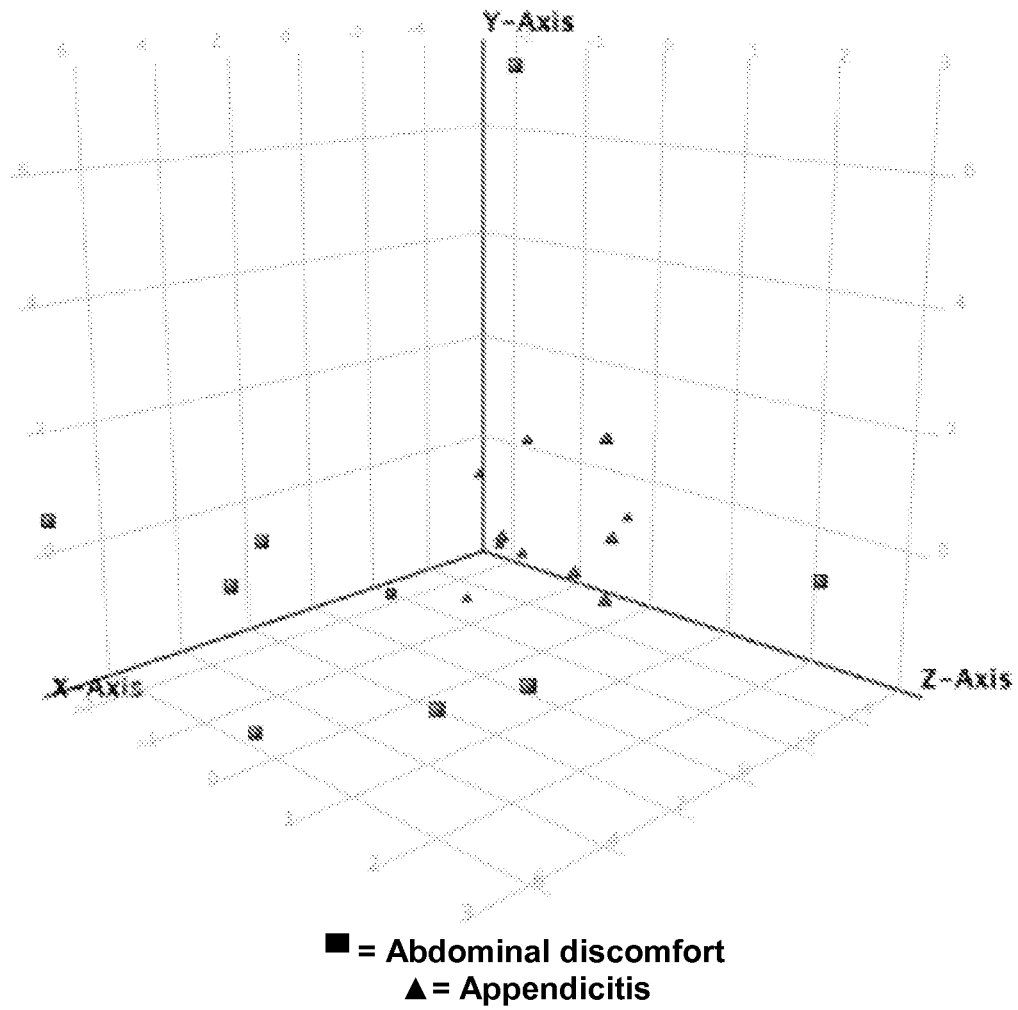
FIG. 3 shows a graph displaying the Partial Least Squares Discriminant (PLSD) Model for classification of appendicitis from RNA biomarkers.
Figure 4:
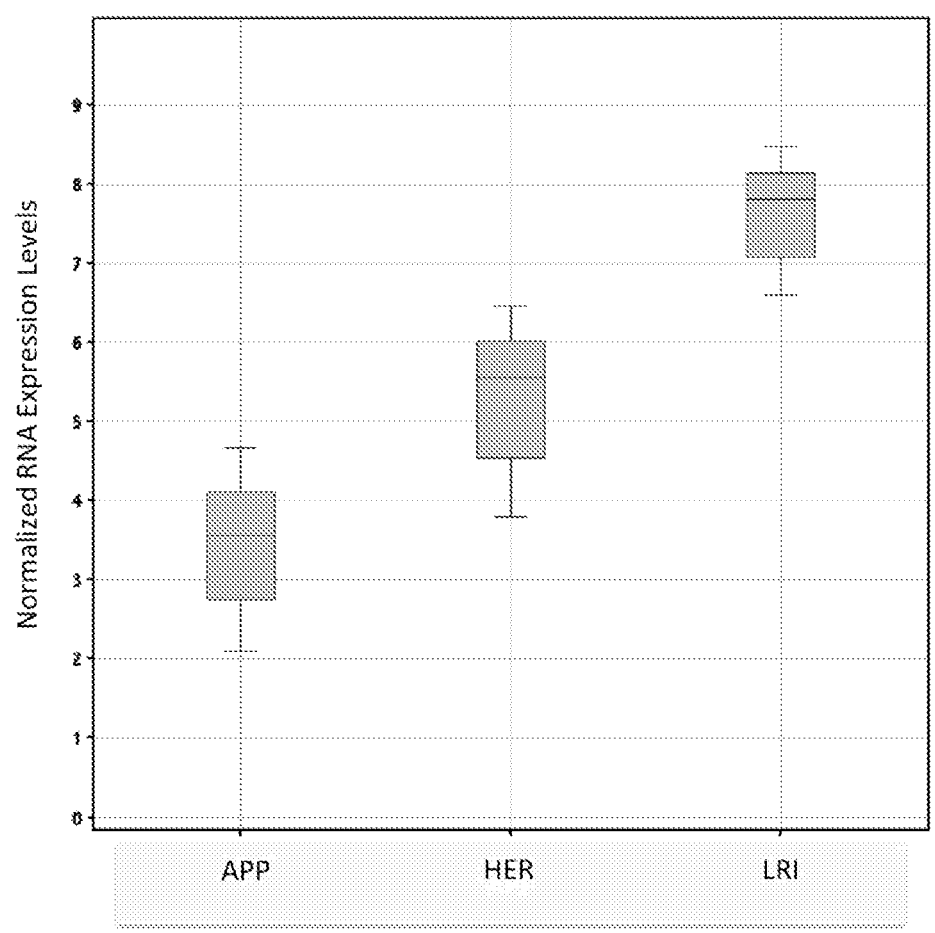
FIG. 4 is a graph showing results of defensins in appendicitis, hernia, and lower respiratory infection patients.

The PLSD model built on the 37 DEG list, was 100% accurate and specific within the discovery set, which is not surprising given the ability of PLSD models to accurately 'fit' data to outcomes. As shown in FIG. 3, the first 3 latent factors in the PLSD model demonstrate tight clustering of the appendicitis patients (▲) distinct from patients presenting with other abdominal pain (■). Clearly, 7 of 9 abdominal patients can be discriminated by only the first latent factor (t0, X-axis). Two abdominal patients, one with a GI bleed and one with diverticulitis, are poorly discriminated by the t0 latent factor shown in the X-axis, but are readily discriminated by one of the two other factors (Y or Z axis). To determine whether all 37 transcripts were necessary for prediction, 16 transcripts with a loading of >0.2 in the PLSD model were used to rebuild a new PLSD prediction model (Table 3, above). This smaller model, which omitted the defensins, remained quite strong, predicting 100% of abdominal cases, 90.9% of appendicitis cases, for an overall accuracy of 95%.

Based on these data, a highly predictive model can be generated by observing expression level patterns utilizing as few as 3 RNA transcripts. Of course the more levels that are measured, the more sensitive and predictive the patterns become. Accordingly, the present invention can use the pattern generated from 3 or more RNA transcripts, 4 or more RNA transcripts, 5 or more RNA transcripts, 6 or more RNA transcripts, 7 or more RNA transcripts, 8 or more RNA transcripts, 9 or more RNA transcripts, 10 or more RNA transcripts, 12 or more RNA transcripts, 14 or more RNA transcripts, or 16 or more RNA transcripts. The only minimum is that the number and selection of transcripts define a pattern that distinguishes appendicitis from other causes of abdominal pain. In embodiments, the method is at least 75% accurate, for example at least 80% accurate, at least 90% accurate, or at least 95% accurate.

FIG. 3 shows a graph displaying the Partial Least Squares Discriminant (PLSD) Model for classification of appendicitis from RNA biomarkers. In FIG. 3, DEGs were analyzed by PLSD to compose a classification model for appendicitis based on RNA biomarkers in blood. The 3D plot shows the 20 patients in the discovery set as partitioned by the first 3 of 4 latent factors in the PLSD model. The ■ represent abdominal pain patients (n=9), and ▲ shows the cluster of appendicitis patients (n=1), as a function of the t0 latent factor (X-axis), the t1 factor (Y-axis), and the t2 factor (Z-axis). The majority of patients (7/9) are accurately classified by the t0 component alone.

Validation of PLSD Prediction Model in Unrelated Samples.

To determine the robustness of the prediction model, a separate group of patients derived from the same overall cohort were similarly processed for whole blood RNA, and hybridized independently to Illumina HT 12v4 Beadchip arrays. With only minimal normalization to correct for minor loading and hybridization differences, the PLSD prediction model was applied to the normalized values for the 37 transcripts in the model. The PLSD prediction model correctly identified 8 of 9 true appendicitis patients (88.9%) and predicted 3 of 4 patients (75%) with hernias as being 'abdominal pain'. Nearly 90% sensitivity in an unrelated cohort quantified on a different microarray run is encouraging toward the potential robustness of the model. Notably, the PLSD model includes no clinical variables, such as fever or white cell count.

Behavior of the RNA Biomarkers in Non-Appendicitis Infections.

Figure 5:
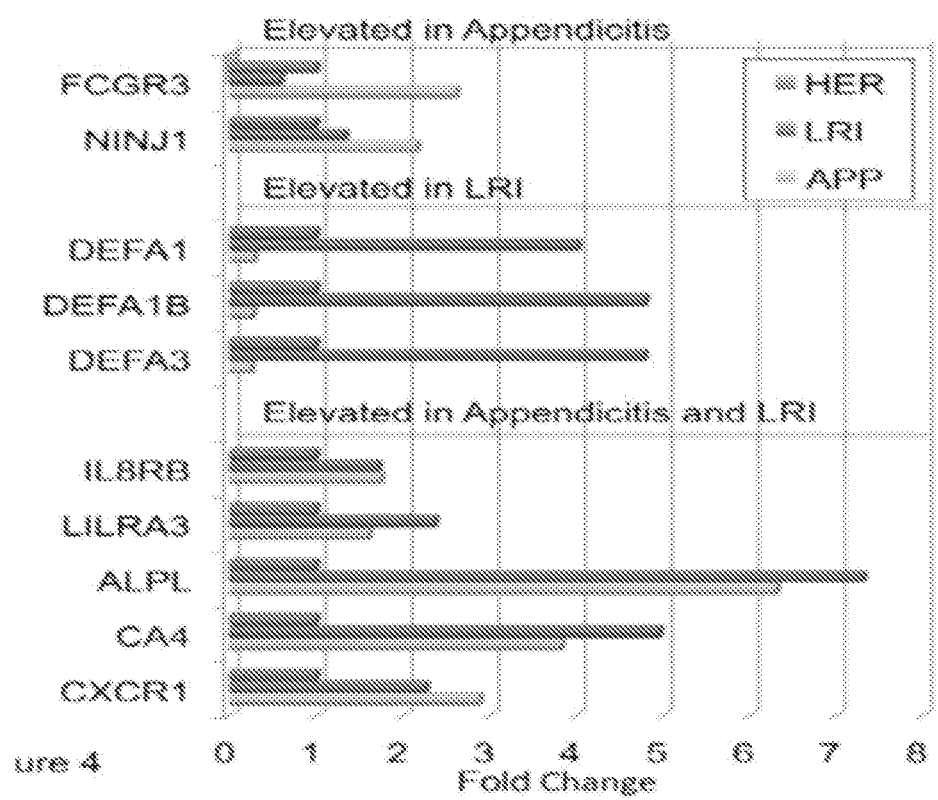
FIG. 5 shows the behavior of selected transcripts in a validation cohort.

In 5 patients clinically diagnosed with LRI, which were not included in PLSD training, the model predicts 4 of 5 as appendicitis (80%), suggesting that the model may be sensitive to generalized infectious or inflammatory signals in blood. Using the 16 DEG model, only 60% were diagnosed as appendicitis. As shown in FIG. 5, some transcripts, such as FCGR3 and NINJ1, were relatively selectively elevated in APP, but not LRI. Other transcripts, especially defensins, were much more sensitive to LRI than APP, showing 4-5 fold elevations in LRI versus HER, and 20-fold elevations in LRI vs APP. Most transcripts, as demonstrated by IL8Rß, LILRA3, and ALPL, showed roughly similar changes in LRI and APP. Of the 37 transcripts, 10 are relatively selective for APP, 8 are selective for LRI, and 19 behave similarly in both APP and LRI.

FIG. 5 shows graphs displaying the behavior of DEG biomarkers in a validation cohort. In FIG. 5, the 37 DEG biomarker set was applied to transcript expression levels in unrelated patients presenting at the ER for either appendicitis (APP, green bars), lower respiratory infection (LRI, red bars), or hernias (HER, blue bars). Representative transcripts, such as Fc gamma receptor 3 (FCGR3) and ninjurin 1 (NINJ1) are shown, in which the transcript behaves with relatively selective induction in APP, relative to HER or LRI. Conversely, transcripts in the defensin family (DEFA1, DEFA3), are significantly elevated in HER patients, relative to APP, but are strikingly induced in LRI patients. Most transcripts, such as alkaline phosphatase (ALPL) and the IL8 receptors (IL8RB, CXCR1), were induced in both APP and LRI patients.

Discussion

Currently, there are no FDA-approved serum or urine biomarkers for abdominal pain or appendicitis. As noted earlier, abdominal pain is one of the most common complaints in the ED, and thus blood biomarkers represent an important unmet need in clinical medicine. In this discovery and validation study, we have identified a small set of RNA transcripts associated with appendicitis. Overall, a prediction model built on these markers was able to differentiate appendicitis from other forms of intra-abdominal pathology, such as diverticulitis and hernias. Appendicitis is thought to be an inflammatory disease, similar to diverticulitis or colitis; however, there was differing activation of certain mRNA biomarkers between these conditions. Furthermore, the 37 DEG markers do not correlate with white blood cell count, per se, but a careful examination of the transcripts suggests that the RNA biomarkers may be measuring the activation state of immune cells, especially neutrophils.

The pattern of transcriptome changes in blood may help to refine our understanding of the etiology and progression of acute appendicitis, as shown schematically in FIG. 6. The classic explanation for appendicitis is that a fecalith or lymphoid hyperplasia block the outflow of the appendix, resulting in obstruction and ischemia [28]. Outflow obstruction may produce local changes that favor undesirable changes in the appendix microbiome. Several recent studies, including next-generation sequencing (NGS) of the 16S regions of the microbiome, have suggested that relatively selective changes in fusobacteria species are associated with appendicitis [29-32]. Fusobacteria, a type of gram-negative bacteria, can induce toxicity in adjacent host cells, and colitis-like symptoms in mice, potentially by producing butyric acid (butyrate) [33]. RT-PCR analysis confirms that inflamed appendix tissue has elevated α-defensin and IL-8 mRNA levels [34]. Likewise, *Fusobacterium nucleatum* biofilms stimulate IL-8 production in human oral epithelium cell lines [35] and *Fusobacterium necrophorum* induces IL-8 production in cultured mesothelial cells [36].

FIG. 6 shows a schematic of a model of appendicitis biomarker pathophysiology. It is believed that compacted fecal bodies, termed fecaliths, may occlude the outflow tract of the appendix, causing inflammatory conditions that are conducive to infection in the appendix. Microbiome analysis of inflamed appendices typically indicates a predominance of biofilm-forming bacteria, such as fusobacteria. The biofilm protects the bacteria from antibiotics, and from direct immune attack, but soluble factors produced by the bacteria, such as LPS (endotoxins) and butyrate, or IL-8, can diffuse into adjacent lymphatic and circulatory beds to activate neutrophils. The primed neutrophils respond with elevated transcript levels of alkaline phosphatase (ALPL), interleukin-8 receptor beta (IL8Rß) and related biomarkers of local infection. Background images of appendix and neutrophil courtesy of Blausen.com staff, *Wikiversity Journal of Medicine*.

Thus, the absence of elevated α-defensin transcripts in the presence of elevated levels of mRNA for both IL-8 receptors suggests that circulating immune cells are primed by IL-8 produced in the inflamed appendix. However, it seems likely that the immune cells are not directly contacting the bacterial infection, which would elevate defensins, as demonstrated clearly in the LRI patients.

In addition to the IL-8 receptors, several other transcripts appear to be plausible biomarkers of localized inflammation. Notably, ALPL, along with IL8RB/CXCR2, was identified as an expression biomarker of asthma inflammatory subtypes [37]. In addition to these interesting innate immune markers, the results revealed unexpected changes in the ribosomal system. Humans utilize 4 ribosomal RNAs, which are non-coding (5S, 5.8S, 18S, 28S), and ~80 ribosomal proteins to build multimeric translation complexes. Additionally, there are ~2000 ribosomal protein pseudogenes, which are thought to derive from inactivated duplications, but may be processed to varying degrees, and could have regulatory functions [38]. Transcripts for 18S and 28S, both originating from multiple 45S genes, were increased in the appendicitis blood RNA, which could be due to both increased transcription from active rDNA genes [39], as well engagement of previously inactive rDNA transcription units [26]. Conversely, most of the coding transcripts, such as RPLP1 and RPS26, were decreased in the blood of appendicitis patients. Because the specific pattern of ribosomal proteins defines the type of RNAs that are engaged and translated [40], it is possible that the translational machinery is being re-geared to adapt to a new demand. Unexpectedly, most of the poorly annotated transcripts mapped to ribosomal protein pseudogenes, suggesting that either the probesets are incorrectly detecting a change in coding ribosomal protein transcripts, or the pseudogenes are somehow regulated in conjunction with the reconfigured translational machinery. Conceptually, the pattern of chemokine, defensin, stress-related, and ribosomal processing changes is consistent with the immune system being 'primed' as the immune cells pass through an inflammatory field created by a localized biofilm infection.

Other investigators have sought to develop protein biomarkers for appendicitis in the blood, such as bilirubin [41], C-reactive protein (CRP) [42], and pro-calcitonin (PCT) [43]. However, recent comparisons of these biomarkers had difficulty improving on a purely clinical prediction model, such as the Alvarado score (ROC=0.74, vs CRP=0.61, PCT=0.69) [44]. Recently, a combination of WBC, CRP, and MRP8/14 (S100A8/S100A9) was shown to be 96% sensitive, but 43% specific for acute appendicitis [42]. Likewise, a multivariate model built on plasma protein levels of serum amyloid (SAA), myeloperoxidase (MPO), and MMP9 was less diagnostic than a largely clinical model (ROC=0.71 vs 0.91 clinical model) [45].

While RNA-based diagnostic tests are currently on the market for breast cancer progression (MammaPrint, OncoType Dx), transplant rejection (AlloMap), and coronary artery disease (CorusCAD), this is the first report to assess blood RNA as a potential biomarker of appendicitis. Among the strengths of the present approach is that the test and validation sets included controls for surgical, inflammatory, and infectious factors. Further, the RNA profiling was broad and largely unbiased, and detected the same key pathways in the test and validation study.

Genome-wide RNA transcript profiling is thus demonstrated as being capable of identifying biomarkers of appendicitis. The detected biomarkers are consistent with prior published evidence that fusobacteria biofilms in the appendix may be an important putative mechanism in appendicitis.

By assaying the RNA levels by microarray analysis, alternative methods of assaying RNA levels can be applied in the steps of this invention. Examples of alternative methods including are real-time RT-PCR, real-time PCR, quantitative RT-PCR, qPCR, RT-PCR array, RNA sequencing (RNA-Seq), northern blot, and serial analysis of gene expression (SAGE), measuring protein expression.

Patterns of RNA levels define biomarkers that identify appendicitis. Differential expression of RNA levels of a gene often coincide with differential expression levels of the resultant proteins translated from the RNA. For this reason, measuring the protein expression level patterns that correlate to the identified differentially expressed genes is an alternative method of diagnosing appendicitis. Protein expression levels can be measured from serum samples by a number of means including western blot, enzyme-linked immunosorbent assay (ELISA), mass spectrometry, and other means that utilize antibody detection of proteins. Similar methods of testing as described for the RNA biomarkers can be used by replacing RNA measurement with protein measurement and determining suitable patterns. According to his embodiment, measuring the protein expression level patterns will diagnose appendicitis. In some embodiments, antibodies against specific proteins can be generated and used to measure protein expression levels.

REFERENCES FOR BACKGROUND AND EXAMPLE 1

1. Bhuiya F, Pitts S, McCaig L (2010) Emergency Department visits for chest pain and abdominal pain: United States, 1999-2008. CDC, NCHS Data Brief 43.
2. Charfi S, Sellami A, Affes A, Yaich K, Mzali R, et al. (2014) Histopathological findings in appendectomy specimens: a study of 24,697 cases. Int J Colorectal Dis 29: 1009-1012.
3. Drake F T, Florence M G Johnson M G, Jurkovich G J, Kwon S, et al. (2012) Progress in the diagnosis of appendicitis: a report from Washington State's Surgical Care and Outcomes Assessment Program. Ann Surg 256: 586-594.

4. Seetahal S A, Bolorunduro O B, Sookdeo T C, Oyetunji T A, Greene W R, et al. (2011) Negative appendectomy: a 10-year review of a nationally representative sample. The American Journal of Surgery 201: 433-437.
5. Kirkil C, Karabulut K, Aygen E, Ihan Y S, Yur M, et al. (2013) Appendicitis scores may be useful in reducing the costs of treatment for right lower quadrant pain. Ulus Travma Acil Cerrahi Derg 19: 13-19.
6. Memon Z A, Irfan S, Fatima K, Iqbal M S, Sami W (2013) Acute appendicitis: diagnostic accuracy of Alvarado scoring system. Asian J Surg 36: 144-149.
7. Teixeira P G, Demetriades D (2013) Appendicitis: changing perspectives. Adv Surg 47: 119-140.
8. Poortman P, Oostvogel H J M, Bosma E, Lohle P N M, Cuesta M A, et al. (2009) Improving Diagnosis of Acute Appendicitis: Results of a Diagnostic Pathway with Standard Use of Ultrasonography Followed by Selective Use of CT. Journal of the American College of Surgeons 208: 434-441.
9. Collins G B, Tan T J, Gifford J, Tan A (2014) The accuracy of pre-appendectomy computed tomography with histopathological correlation: a clinical audit, case discussion and evaluation of the literature. Emerg Radiol 21: 589-595.
10. Rosen M P, Ding A, Blake M A, Baker M E, Cash B D, et al. (2011) ACR Appropriateness Criteria® Right Lower Quadrant Pain—Suspected Appendicitis. Journal of the American College of Radiology 8: 749-755.
11. Ahn S, group L (2014) LOCAT (low-dose computed tomography for appendicitis trial) comparing clinical outcomes following low- vs standard-dose computed tomography as the first-line imaging test in adolescents and young adults with suspected acute appendicitis: study protocol for a randomized controlled trial. Trials 15: 28.
12. Miglioretti D L, Johnson E, Williams A, Greenlee R T, Weinmann S, et al. (2013) The use of computed tomography in pediatrics and the associated radiation exposure and estimated cancer risk. JAMA Pediatr 167: 700-707.
13. Wai S, Ma L, Kim E, Adekunle-Ojo A (2013) The utility of the emergency department observation unit for children with abdominal pain. Pediatr Emerg Care 29: 574-578.
14. Seo H, Lee K H, Kim H J, Kim K, Kang S-B, et al. (2009) Diagnosis of Acute Appendicitis With Sliding Slab Ray-Sum Interpretation of Low-Dose Unenhanced CT and Standard-Dose IV Contrast-Enhanced CT Scans. American Journal of Roentgenology 193: 96-105.
15. Kim S Y, Lee K H, Kim K, Kim T Y, Lee H S, et al. (2011) Acute Appendicitis in Young Adults: Low-versus Standard-Radiation-Dose Contrast-enhanced Abdominal CT for Diagnosis. Radiology 260: 437-445.
16. Keyzer C, Tack D, de Maertelaer V, Bohy P, Gevenois P A, et al. (2004) Acute Appendicitis: Comparison of Low-Dose and Standard-Dose Unenhanced Multi-Detector Row CT. Radiology 232: 164-172.
17. Huang da W, Sherman B T, Lempicki R A (2009) Systematic and integrative analysis of large gene lists using DAVID bioinformatics resources. Nat Protoc 4: 44-57.
18. Subrahmanyam Y V, Yamaga S, Prashar Y, Lee H H, Hoe N P, et al. (2001) RNA expression patterns change dramatically in human neutrophils exposed to bacteria. Blood 97: 2457-2468.
19. Kubo T, Yamashita T, Yamaguchi A, Hosokawa K, Tohyama M (2002) Analysis of genes induced in peripheral nerve after axotomy using cDNA microarrays. J Neurochem 82: 1129-1136.
20. Watson R P, Lilley E, Panesar M, Bhalay (Langridge S, et al. (2012) Increased prokineticin 2 expression in gut inflammation: role in visceral pain and intestinal ion transport. Neurogastroenterol Motil 24: 65-75, e12.
21. Pike A F, Kramer N I, Blaauboer B J, Seinen W, Brands R (2013) A novel hypothesis for an alkaline phosphatase 'rescue' mechanism in the hepatic acute phase immune response. Biochim Biophys Acta 1832: 2044-2056.
22. Poortinga G, Wall M, Sanij E, Siwicki K, Ellul J, et al. (2011) c-MYC coordinately regulates ribosomal gene chromatin remodeling and Pol I availability during granulocyte differentiation. Nucleic Acids Res 39: 3267-3281.
23. Uemura M, Zheng Q, Koh C M, Nelson W G, Yegnasubramanian S, et al. (2012) Overexpression of ribosomal RNA in prostate cancer is common but not linked to rDNA promoter hypomethylation. Oncogene 31: 1254-1263.
24. Congiu M, Slavin J L, Desmond P V (2011) Expression of common housekeeping genes is affected by disease in human hepatitis C virus-infected liver. Liver Int 31: 386-390.
25. Derenzini M, Farabegoli F, Pession A, Novello F (1987) Spatial redistribution of ribosomal chromatin in the fibrillar centres of human circulating lymphocytes after stimulation of transcription. Exp Cell Res 170: 31-41.
26. Haaf T, Hayman D L, Schmid M (1991) Quantitative determination of rDNA transcription units in vertebrate cells. Exp Cell Res 193: 78-86.
27. Huang X, Dai F F, Gaisano (G Giglou K, Han J, et al. (2013) The identification of novel proteins that interact with the GLP-1 receptor and restrain its activity. Mol Endocrinol 27: 1550-1563.
28. Ramdass M J, Young Sing Q, Milne D, Mooteeram J, Barrow S (2015) Association between the appendix and the fecalith in adults. Can J Surg 58: 10-14.
29. Jackson H T, Mongodin E F, Davenport K P, Fraser C M, Sandler A D, et al. (2014) Culture-independent evaluation of the appendix and rectum microbiomes in children with and without appendicitis. PLoS One 9: e95414.
30. Zhong D, Brower-Sinning R, Firek B, Morowitz M J (2014) Acute appendicitis in children is associated with an abundance of bacteria from the phylum Fusobacteria. J Pediatr Surg 49: 441-446.
31. Guinane C M, Tadrous A, Fouhy F, Ryan C A, Dempsey E M, et al. (2013) Microbial composition of human appendices from patients following appendectomy. MBio 4.
32. Swidsinski A, Dorffel Y, Loening-Baucke V, Theissig F, Ruckert J C, et al. (2011) Acute appendicitis is characterised by local invasion with *Fusobacterium nucleatum/necrophorum*. Gut 60: 34-40.
33. Ohkusa T, Okayasu I, Ogihara T, Morita K, Ogawa M, et al. (2003) Induction of experimental ulcerative colitis by *Fusobacterium varium* isolated from colonic mucosa of patients with ulcerative colitis. Gut 52: 79-83.
34. Arlt A, Bharti R, Ilves I, Hasler R, Miettinen P, et al. (2013) Characteristic changes in microbial community composition and expression of innate immune genes in acute appendicitis. Innate Immun.
35. Peyyala R, Kirakodu S S, Novak K F, Ebersole J L (2012) Oral microbial biofilm stimulation of epithelial cell responses. Cytokine 58: 65-72.
36. Zeillemaker A M, Hoynck van Papendrecht A A, Hart M H, Roos D, Verbrugh H A, et al. (1996) Peritoneal interleukin-8 in acute appendicitis. J Surg Res 62: 273-277.

37. Baines K J, Simpson J L, Wood L, Scott R, Fibbens N, et al. (2014) Sputum gene expression signature of 6 biomarkers discriminates asthma inflammatory phenotypes. J Allergy Clin Immunol 133: 997-1007.
38. Zhang Z, Harrison P, Gerstein M (2002) Identification and analysis of over 2000 ribosomal protein pseudogenes in the human genome. Genome Res 12: 1466-1482.
39. Shiune C N, Nematollahi-Mahani A, Wright A P (2014) Myc-induced anchorage of the rDNA IGS region to nucleolar matrix modulates growth-stimulated changes in higher-order rDNA architecture. Nucleic Acids Res 42: 5505-5517.
40. Remacha M, Jimenez-Diaz A, Bermejo B, Rodriguez-Gabriel M A, Guarinos E, et al. (1995) Ribosomal acidic phosphoproteins P1 and P2 are not required for cell viability but regulate the pattern of protein expression in *Saccharomyces cerevisiae*. Mol Cell Biol 15: 4754-4762.
41. D'Souza N, Karim D, Sunthareswaran R (2013) Bilirubin; a diagnostic marker for appendicitis. Int J Surg 11: 1114-1117.
42. Huckins D S, Simon H K, Copeland K, Spiro D M, Gogain J, et al. (2013) A novel biomarker panel to rule out acute appendicitis in pediatric patients with abdominal pain. Am J Emerg Med 31: 1368-1375.
43. Kaya B, Sana B, Eris C, Karabulut K, Bat O, et al. (2012) The diagnostic value of D-dimer, procalcitonin and CRP in acute appendicitis. Int J Med Sci 9: 909-915.
44. Wu J Y, Chen H C, Lee S H, Chan R C, Lee C C, et al. (2012) Diagnostic role of procalcitonin in patients with suspected appendicitis. World J Surg 36: 1744-1749.
45. Andersson M, Ruber M, Ekerfelt C, Hallgren H B, Olaison G, et al. (2014) Can new inflammatory markers improve the diagnosis of acute appendicitis? World J Surg 38: 2777-2783.

Example 2: Confirmation of Microarray Results

Figure 7:
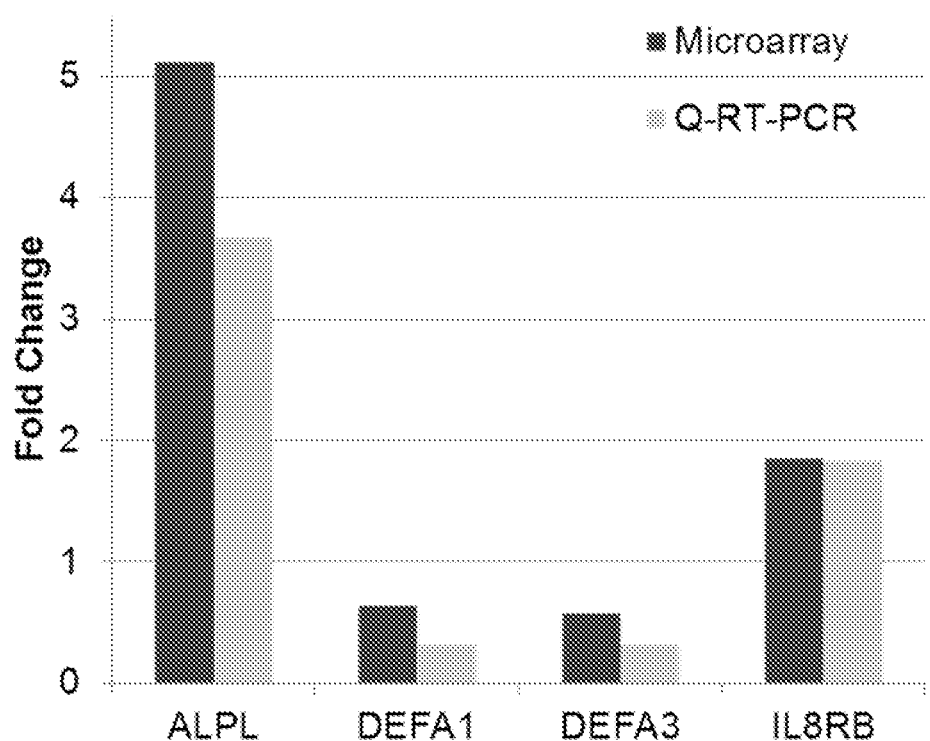
FIG. 7 shows a graph showing microarray and quantitative reverse-transcription polymerase chain reaction results for 3 genes differentially expressed in subjects with appendicitis.

Quantitative Real Time Polymerase Chain Reaction (Q-RTPCR) was sued to confirm the microarray results from Examples 1 and 2. FIG. 7 shows Q-RTPCR results for 3 genes: ALPL, DEFA1/3 and IL8RB. As seen in FIG. 7, results obtained from Q-RTPCR parallel the results obtained from the microarray assays.

Methods

1) RNA Purification:

1.1) For validation studies, the RNA purified for microarray analysis was used. In new samples, or other embodiments, the sample of blood must be collected in an appropriate RNA stabilizer. In the present studies, Tempus tubes were used. Other stabilizers could be used, but it is possible that the specific transcripts levels of expression or their magnitude, could be different depending upon the RNA Blood tubes used and their RNA stabilizers. From the Tempus tubes, the manufacturer's instruction and reagents for column purification of RNA was used. However, technically, both DNA and RNA are purified.

2) DNAse Treatment:

2.1) To remove the DNA, which will confuse the quantitation of RNA, the sample is treated with Turbo DNA-Free™ Kit (ThermoFisher Sci, Cat. No AM1907). We used up to 5 ug total RNA/DNA treated with 2 units/μL of TurboDNAse for 30 min at 37° C. The inactivation of DNAse was performed using the "Inactivation Reagent" (IR) provided in the kit at 0.2× volume of the total reaction, typically 20 μL of IR for 100 μL of DNase treatment. The IR contains an affinity capture reagent recognizing the TurboDNAse, thereby removing it from solution, and eluting relatively pure RNA. A variety of DNAse removal strategies are well known to anyone skilled in the art. In particular, it is common to heat-inactivate the DNAse. While probably acceptable, it has not been specifically tested, and we cannot exclude the possibility that this would be a source of variation (SOV).

2.2) The DNase treated RNA is further purified in Qiagen RNAeasy MiniElute kit (Qiagen, Cat. No. 74204) on columns The RNA quantity is assessed by absorbance at 260 nm (NanoDrop) and the quality is assessed by the ratio of absorbance at 260 nm (RNA) to 280 nm (protein). A ratio (260/280) greater than 1.8 is desirable if measured in water, and greater than 2.0 if measured in water buffered with Tris/EDTA (TE).

3) Complementary DNA (cDNA) Synthesis:

3.1) The purified RNA was converted to cDNA using reverse transcriptase (RT) contained in the iScript cDNA Synthesis kit from Bio-Rad Laboratories (Cat. No. 170-8891). There are published reasons to believe that the type of RT enzyme could affect the efficiency of cDNA synthesis, and therefore, the measured levels of specific transcripts by qRT-PCR. In particular, the presence or absence of the RNAse H activity in the RT enzyme might be a relevant SOV. The iScript cDNA kit reverse transcriptase contains RNase H enzymes for degradation of RNA template in the amplification process.

4) PCR Probe Selection:

4.1) Sense and antisense probes for PCR were selected using the cDNA sequences extracted from Genbank accession numbers disclosed in Table 1. The cDNA sequences were analyzed by Geneious software to identify primers with matching melting temperatures (Tm) of 60° C. under standard RT-PCR conditions. The primers identified and used are shown in Table 1.

4.2) In this example, 6 transcripts were targeted for qRT-PCR quantitation. Four of these transcripts (ALPL, DEFA1, DEFA3, IL8RB) were selected from the 16 g and 37 g lists of DEGs that are diagnostic of appendicitis. Two other transcripts, ACTB and SpiB, were used as transcripts which should not vary according to appendicitis status, and thus are considered 'invariant' for this example.

4.3) For each transcript-specific reaction, additional samples are prepared in which the pooled control cDNA (Con) is used at higher, and lower quantities, typically in 10-fold steps, to create a standard dose-response curve for each primer pair. This curve confirms that the qPCR is able to detect higher and lower transcript levels, and is used to convert the Ct to a relative abundance measure as described below.

5) qRT-PCR Conditions:

5.1) A standard amount of cDNA (0.20-0.25 ng) from the patient samples, or a pooled control sample (Con), was combined with a fixed amount of the transcript-specific primer pairs (1.25 μM) and a master mix SSOAdvanced™ Universal SYBR® Green Supermix (Bio-Rad, Cat. No.: 172-5274) containing a mix of antibody-mediated hot-start Sso7d fusion polymerase, dNTPs, MgCl2, enhancers, stabilizers, a blend of passive reference dyes (including ROX and fluorescein) and SYBR Green fluorescent dye, which reports the level of PCR amplimer that is present after each amplification cycle. There are numerous acceptable ways to quantitate PCR amplimer levels, including, but not limited to, SYBR Green, EVA green, and fluorescently-labeled internal probes commonly referred to TaqMan probes. Another envisioned embodiment of the invention would be to quantitate the transcript levels using droplet digital PCR (ddPCR, BioRad) or hybrid-based transcript counting methods, such as Nanostring.

In this example, we employed the BioRad SSOAdvanced kit reagents. Each transcript-specific primer pair and sample, cDNA was analyzed in a separate well of a 384-well plate in duplicate for each primer pair. Thus, for a given patient sample, 12 qPCR reactions were performed (6 primer pairs, each in duplicate). The mixture containing probes, cDNA sample, and PCR reagents, including fluorescent dye, in a final volume of 14 µl, were loaded using the automatic liquid handler (Eppendorf epMotion® 5770) subjected to thermocycling as described below.

5.2) The mixture of these reagents was incubated in a BioRad CFX384™ Real-Time System with C1000™ thermocycler using a temperature program of: 2 min at 98° C., followed by 45 amplification cycles of 5 sec at 98° C., and 10 sec @ 60° C., finalized with 10 sec @ 75° C. and 4 sec @ 95° C. dissociation stage. After each cycle, the level of fluorescence of the SYBR Green dye bound to dsDNA amplimers was quantified by stimulation with appropriate filters for excitation and emission. The reaction was cycled 40 times and then held at 4° C. after the last cycle.

6) Data Analysis:

6.1) The real-time quantitative PCR instruments measure fluorescence generated by the amplimer/dye complex after each cycle of amplification. Because the amounts of primers and free nucleic acids are limiting, these reaction reach a saturated maximum of fluorescence typically prior to 40 cycles of amplification. The number of cycles observed to reach half-maximal fluorescent intensity is said to be a Cycle Threshold (Ct) of Cycle Quantity (Cq) which is inversely correlated to the amount of transcript cDNA in the reaction. Thus, the higher the level of target cDNA present, the fewer cycles will be needed to reach a given Ct. In practice, there are numerous acceptable methods to stipulate the Ct based on the fluorescence curve, and as long as the Ct is applied uniformly to the samples in each transcript-specific reaction, including the Con samples, then the results should be informative for the present purposes.

6.2) The Ct values for each reaction are converted to a relative abundance (RA) of the transcript by interpolation to the standard curve for each primer pair. That RA level per duplicate PCR tube is then averaged for the 2 duplicates, and then adjusted by the abundance of the 'invariant' transcript levels. A very large number of invariant transcripts would be acceptable, and some that are commonly used by those skilled in the art include: glyceraldehyde 3-phosphate dehydrogenase (GAPDH), ß-actin (ACTB), hypozanthine phosphoribosyltransferase 1 (HPRT), and 18S ribosomal RNA. In the present invention, it was empirically determined that ACTB provided efficient normalization, but the invention is not constrained by the method of normalization.

6.3) The RA levels of the 4 diagnostic transcripts were combined in the following way to predict the outcome of appendicitis:

6.3.1) To account for arbitrary nature of RA value, it was normalized to a percentile of the mean value in the entire run of 36 samples, yielding a % RA value, where 1.00 would be equal to the mean value of that transcript target.

6.3.2) Using the % RA value, the diagnostic goal is to determine whether the ALPL and IL8RB levels are increased disproportionately to the DEFA1 levels. In principle, DEFA3 levels could be used, or a combination of DEFA1 and DEFA3 levels, but for simplicity DEFA1 levels were found to be adequate. Thus, the ratio of % RA of ALPL (% ALPL) to % RA of DEFA1 (% DEFA1), and the ratio of % RA of IL8RB (% IL8RB) to % DEFA1 were computed to yield % ALPL/% DEFA1 and % IL8RB/% DEFA1. Those two values were averaged to compute the App Score. In this series of 36 patient samples, the App Score had a range of 0.04-44.7.

Thus, to summarize,

App Score=[(% ALPL/% DEFA1)+(% IL8RB/% DEFA1)]/2

Another construction is App Score=[(% ALPL+% IL8RB)/2]/% DEFA1

6.3.3) On both logical grounds, and empirical observation, if the App Score is >1 then the normalized ALPL and IL8RB levels are higher than DEFA1 levels and this is taken as diagnostic of an increased likelihood of appendicitis. In actual practice, there would be numerous mathematical and technical means to arrive at a similar assessment of the relative levels of these predictive transcripts identified in the 16 g or 37 g lists.

6.3.4) To test the diagnostic ability of the App Score, it was converted to a scale of 1-10 which is a common metric range used in the Receiver-Operator Characteristic (ROC) statistic. The conversion from App Score to App Level (1-10) was achieved with the following conversion table:

TABLE 6

Conversion Table for converting App Score to App Level

| Coding Key App Score | App Level |
|---|---|
| <0.2 | 1 |
| <0.4 | 2 |
| <0.6 | 3 |
| <0.8 | 4 |
| <1.0 | 5 |
| <2 | 6 |
| <4 | 7 |
| <8 | 8 |
| <16 | 9 |
| >16 | 10 |

Figure 8:
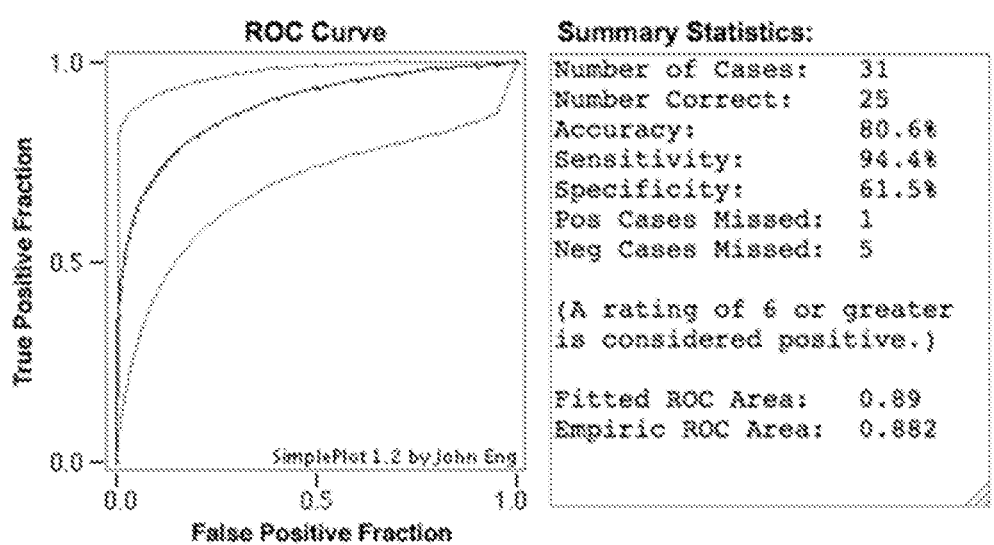
FIG. 8 shows a Receiving Operating Characteristic (ROC) curve with data from 3 gene transcripts.

As discussed above, a predictive test was built taking the data from FIG. 7. A very simple way to predict Appendicitis (Appy) using only 3 gene transcripts (IL8RB, DEFA1, ALPL) and one control transcript (Actin) was developed. FIG. 8 shows a graph of the ROC curve with sensitivity and specificity. In practice, the test gives a score from 1 to 10, where 5-6 is about a 50% risk of Appy, and a score above 7 indicates likely Appy.

The true presence or absence of appendicitis was known from clinical analysis and was scored as a binary variable where 0=absent, 1=appendicitis. Five of the 36 patients were excluded from analysis because they had a clinical diagnoses of lower respiratory infection, which is unrelated to the present invention. An App Score >1, which is an App Level of 6 or greater, was used as a threshold for predicted appendicitis. The predicted outcome (App Level) and the true outcome were used to compute a 'confusion table' and an ROC curve by the method of John Eng: (JROCFIT: Johns Hopkins University, Baltimore, Md. Version 1.0.2, March 2004. URL: http://www.rad.jhmi.edu/ieng/javarad/roc/JROCFITi.html).

The results are shown in FIG. 8, and indicate that overall the accuracy was 80.6%, with 94.4% sensitivity in detecting clinically diagnosed appendicitis.

Example 3: Prediction of Appendicitis from Blood and Urine Samples

Blood and urine samples were collected from emergency department patients with abdominal pain.

Analyte concentrations in plasma and urine samples were measured by immunoassay with commercially available reagents using standard sandwich enzyme immunoassay techniques. A first antibody which binds the analyte is immobilized in wells of a 96 well polystyrene microplate. Analyte standards and test samples are pipetted into the appropriate wells and any analyte present is bound by the immobilized antibody. After washing away any unbound substances, a biotinylated second antibody which binds the analyte is added to the wells, thereby forming sandwich complexes with the analyte (if present) and the first antibody. Following a wash to remove any unbound biotinylated antibody reagent, streptavidin-conjugated horseradish peroxidase is added to the wells. Following another wash, a substrate solution comprising tetramethylbenzidine and hydrogen peroxide is added to the wells. Color develops in proportion to the amount of analyte present in the sample. The color development is stopped and the intensity of the color is measured at 450 nm and 540 nm or 570 nm. An analyte concentration is assigned to the test sample by comparison to a standard curve determined from the analyte standards. Units for all analytes reported herein are ng/mL.

Patients with abdominal pain were determined to have appendicitis (Appy) or not have appendicitis (ABD) by physician diagnosis based in part on a computerized tomography (CT) scan. Protein concentrations in the "Appy" and "ABD" cohorts are compared using the Wilcoxon-Mann-Whitney test. The ability of a protein biomarker to distinguish between the "Appy" and "ABD" patients is determined using receiver operating characteristic (ROC) analysis.

TABLE 7.1

Protein Concentrations in Plasma. P-values for Wilcoxon-Mann-Whitney test are reported.

| | ALPL | | CA4 | | DEFA1 | | DEFA3 | | FCGR3B | | LILRA3 | |
|---|---|---|---|---|---|---|---|---|---|---|---|---|
| | ABD | Appy | ABD | Appy | ABD | Appy | ABD | Appy | ABD | Appy | ABD | Appy |
| 5th percentile | 99.5 | 87.9 | 8.5 | 5.9 | 7.7 | 8.3 | 5.6 | 6.5 | 0.00 | 0.00 | 0.00 | 0.00 |
| 25th percentile | 114.7 | 116.9 | 14.5 | 11.0 | 9.1 | 9.5 | 7.5 | 6.8 | 0.00 | 0.00 | 0.00 | 0.00 |
| Median | 171.2 | 146.1 | 27.5 | 21.0 | 12.2 | 11.4 | 9.1 | 7.1 | 0.00 | 0.00 | 0.53 | 0.00 |
| 75th percentile | 240.5 | 176.8 | 59.4 | 27.1 | 16.2 | 13.6 | 13.2 | 8.4 | 0.44 | 0.34 | 1.76 | 0.93 |
| 95th percentile | 548.4 | 471.6 | 109.5 | 108.1 | 22.9 | 100.4 | 59.1 | 11.1 | 3.49 | 2.43 | 3.78 | 2.75 |
| P | 0.270 | | 0.180 | | 0.606 | | 0.018 | | 0.803 | | 0.205 | |

TABLE 7.2

Protein Concentrations in Urine. P-values for Wilcoxon-Mann-Whitney test are reported.

| | ALPL | | CA4 | | DEFA1 | | DEFA3 | | FCGR3B | | LILRA3 | |
|---|---|---|---|---|---|---|---|---|---|---|---|---|
| | ABD | Appy | ABD | Appy | ABD | Appy | ABD | Appy | ABD | Appy | ABD | Appy |
| 5th percentile | 0.0 | 0.0 | 0.00 | 0.00 | 0.0 | 1.7 | 0.0 | 0.0 | 0.00 | 0.00 | 0.00 | 0.00 |
| 25th percentile | 0.3 | 0.0 | 0.00 | 0.00 | 2.9 | 4.8 | 0.4 | 0.0 | 0.00 | 0.00 | 0.00 | 0.00 |
| Median | 2.6 | 1.9 | 0.00 | 0.00 | 10.8 | 10.6 | 1.1 | 0.3 | 0.02 | 0.00 | 0.00 | 0.00 |
| 75th percentile | 7.7 | 4.5 | 0.30 | 0.52 | 33.2 | 13.4 | 3.9 | 1.0 | 2.69 | 0.08 | 0.35 | 0.00 |
| 95th percentile | 63.4 | 7.9 | 1.31 | 0.70 | 809.1 | 24.9 | 25.9 | 2.4 | 25.82 | 0.39 | 3.34 | 0.37 |
| P | 0.047 | | 0.295 | | 0.065 | | 0.034 | | 0.230 | | 0.691 | |

TABLE 8.1

Area under the receiver operating characteristic curve (AUC) of proteins in plasma. An AUC < 0.5 indicates protein concentrations are generally lower in patients with appendicitis. P-values for the null hypothesis of AUC = 0.5 are reported.

| Assay | Uniprot # | AUC | SE | ABD (no appendicitis) | Appendicitis | p |
|---|---|---|---|---|---|---|
| DEFA3 | P59666 | 0.291 | 0.095 | 45 | 11 | 0.027 |
| CA4 | P22748 | 0.369 | 0.099 | 45 | 11 | 0.183 |
| LILRA3 | Q8N6C8 | 0.376 | 0.099 | 45 | 11 | 0.209 |
| ALPL | P05186 | 0.396 | 0.099 | 45 | 11 | 0.295 |
| DEFA1 | P59665 | 0.462 | 0.099 | 45 | 11 | 0.698 |
| FCGR3B | O75015 | 0.492 | 0.098 | 45 | 11 | 0.934 |

TABLE 8.2

Area under the receiver operating characteristic curve (AUC) of proteins in urine. An AUC < 0.5 indicates protein concentrations are generally lower in patients with appendicitis. P-values for the null hypothesis of AUC = 0.5 are reported.

| Assay | Uniprot # | AUC | SE | ABD (no appendicitis) | Appendicitis | P |
|---|---|---|---|---|---|---|
| DEFA3 | P59666 | 0.293 | 0.095 | 45 | 11 | 0.029 |
| ALPL | P05186 | 0.307 | 0.096 | 45 | 11 | 0.044 |
| DEFA1 | P59665 | 0.319 | 0.097 | 45 | 11 | 0.061 |
| FCGR3B | O75015 | 0.393 | 0.099 | 45 | 11 | 0.281 |
| CA4 | P22748 | 0.404 | 0.099 | 45 | 11 | 0.334 |
| LILRA3 | Q8N6C8 | 0.534 | 0.099 | 45 | 11 | 0.729 |

TABLE 9.1

Confusion table and odds ratio for appendicitis using plasma DEFA3. A cutoff concentration of 122 ng/mL is selected corresponding to the 33rd percentile.

| DEFA3 | Adjudication ABD | Appy | Total |
|---|---|---|---|
| <=cutoff | 11 | 8 | 19 |
| >cutoff | 34 | 3 | 37 |
| Total | 45 | 11 | 56 |

Odds ratio (95% CI)=8.2 (1.9-34.2), where Odds ratio=Odds below cutoff/Odds above cutoff.

TABLE 9.2

Confusion table and odds ratio for appendicitis using urine ALPL. A cutoff concentration of 2.47 ng/mL is selected corresponding to the 50th percentile.

| ALPL | Adjudication ABD | Appy | Total |
|---|---|---|---|
| <=cutoff | 19 | 9 | 28 |
| >cutoff | 26 | 2 | 28 |
| Total | 45 | 11 | 56 |

Odds ratio (95% CI)=6.2 (1.3-28.3), where Odds ratio=Odds below cutoff/Odds above cutoff.

TABLE 9.3

Confusion table and odds ratio for appendicitis using urine DEFA1. A cutoff concentration of 10.85 ng/mL is selected corresponding to the 50th percentile.

| DEFA1 | Adjudication ABD | Appy | Total |
|---|---|---|---|
| <=cutoff | 19 | 9 | 28 |
| >cutoff | 26 | 2 | 28 |
| Total | 45 | 11 | 56 |

Odds ratio (95% CI)=6.2 (1.3-28.3), where Odds ratio=Odds below cutoff/Odds above cutoff.

TABLE 9.4

Confusion table and odds ratio for appendicitis using urine DEFA3. A cutoff concentration of 0.33 ng/mL is selected corresponding to the 25th percentile.

| DEFA3 | Adjudication ABD | Appy | Total |
|---|---|---|---|
| <=cutoff | 8 | 7 | 15 |
| >cutoff | 37 | 4 | 41 |
| Total | 45 | 11 | 56 |

Odds ratio (95% CI)=8.1 (2.0-33.1), where Odds ratio=Odds below cutoff/Odds above cutoff.

The individual biomarker assay results obtained from each sample were combined to provide a single result as indicated herein, and the single result treated as an individual biomarker using standard statistical methods. In expressing these combinations, the arithmetic operators such as "x" (multiplication) and "/" (division) are used in their ordinary mathematical sense.

TABLE 10.1

AUC of combinations of 2 plasma proteins. An AUC < 0.5 indicates protein concentrations are generally lower in patients with appendicitis. P-values for the null hypothesis of AUC = 0.5 are reported.

| 2-Marker Combination | AUC | SE | ND | D | p |
|---|---|---|---|---|---|
| ALPL x DEFA3 | 0.285 | 0.094 | 45 | 11 | 0.0224 |
| DEFA3 x LILRA3 | 0.285 | 0.094 | 45 | 11 | 0.0224 |
| CA4 x DBFA3 | 0.319 | 0.097 | 45 | 11 | 0.0612 |
| CA4 x LILRA3 | 0.323 | 0.097 | 45 | 11 | 0.0678 |
| ALPL x CA4 | 0.331 | 0.097 | 45 | 11 | 0.0827 |

TABLE 10.2

AUC of combinations of 2 urine proteins. An AUC < 0.5 indicates protein concentrations are generally lower in patients with appendicitis. P-values for the null hypothesis of AUC = 0.5 are reported.

| 2-Marker Combination | AUC | SE | ND | D | p |
|---|---|---|---|---|---|
| ALPL x DEFA1 | 0.271 | 0.093 | 45 | 11 | 0.0137 |
| ALPL x FCGR3B | 0.281 | 0.094 | 45 | 11 | 0.0195 |
| DEFA1 x DEFA3 | 0.281 | 0.094 | 45 | 11 | 0.0195 |
| ALPL x DEFA3 | 0.288 | 0.094 | 45 | 11 | 0.0247 |
| CA4 x DEFA1 | 0.293 | 0.095 | 45 | 11 | 0.0290 |
| CA4 x DEFA3 | 0.294 | 0.095 | 45 | 11 | 0.0299 |
| LILRA3/DEFA3 | 0.705 | 0.095 | 45 | 11 | 0.0309 |
| LILRA3/ALPL | 0.701 | 0.095 | 45 | 11 | 0.0349 |
| DEFA3 x FCGR3B | 0.307 | 0.096 | 45 | 11 | 0.0441 |
| ALPL x CA4 | 0.308 | 0.096 | 45 | 11 | 0.0453 |
| CA4 x FCGR3B | 0.323 | 0.097 | 45 | 11 | 0.0678 |

TABLE 10.3

AUC of combinations of 1 urine (u) and 1 plasma (p) protein. An AUC < 0.5 indicates protein concentrations are generally lower in patients with appendicitis. P-values for the null hypothesis of AUC = 0.5 are reported.

| 2-Marker Combination | AUC | SE | ND | D | p |
|---|---|---|---|---|---|
| DEFA1(u) x LILRA3(p) | 0.246 | 0.091 | 45 | 11 | 0.0051 |
| DEFA1(u) x CA4(p) | 0.271 | 0.093 | 45 | 11 | 0.0137 |
| ALPL(u) x DEFA3(p) | 0.277 | 0.094 | 45 | 11 | 0.0170 |
| DEFA3(u) x DEFA3(p) | 0.279 | 0.094 | 45 | 11 | 0.0182 |

TABLE 10.3-continued

AUC of combinations of 1 urine (u) and 1 plasma (p) protein. An AUC < 0.5 indicates protein concentrations are generally lower in patients with appendicitis. P-values for the null hypothesis of AUC = 0.5 are reported.

| 2-Marker Combination | AUC | SE | ND | D | p |
|---|---|---|---|---|---|
| DEFA3(u) × LILRA3(p) | 0.280 | 0.094 | 45 | 11 | 0.0189 |
| DEFA1(u) × DEFA3(p) | 0.289 | 0.095 | 45 | 11 | 0.0255 |
| DEFA3(u) × ALPL(p) | 0.291 | 0.095 | 45 | 11 | 0.0272 |
| DEFA3(u) × CA4(p) | 0.299 | 0.095 | 45 | 11 | 0.0349 |
| DEFA1(u) × ALPL(p) | 0.299 | 0.095 | 45 | 11 | 0.0349 |
| FCGR3B(u) × DEFA3(p) | 0.309 | 0.096 | 45 | 11 | 0.0466 |
| ALPL(u) × LILRA3(p) | 0.310 | 0.096 | 45 | 11 | 0.0479 |
| FCGR3B(u) × LILRA3(p) | 0.316 | 0.096 | 45 | 11 | 0.0565 |
| ALPL(u) × ALPL(p) | 0.317 | 0.096 | 45 | 11 | 0.0580 |
| DEFA1(u) × DEFA1(p) | 0.333 | 0.097 | 45 | 11 | 0.0868 |
| DEFA3(u) × DEFA1(p) | 0.333 | 0.097 | 45 | 11 | 0.0868 |
| LILRA3(u)/LILRA3(p) | 0.666 | 0.097 | 45 | 11 | 0.0889 |
| ALPL(u) × CA4(p) | 0.335 | 0.097 | 45 | 11 | 0.0910 |
| DEFA3(u) × FCGR3B(p) | 0.335 | 0.097 | 45 | 11 | 0.0910 |

TABLE 10.4

AUC of combinations of 3 plasma proteins. An AUC < 0.5 indicates protein concentrations are generally lower in patients with appendicitis. P-values for the null hypothesis of AUC = 0.5 are reported.

| 3-Marker Combination | AUC | SE | ND | D | p |
|---|---|---|---|---|---|
| ALPL × CA4 × DEFA3 | 0.287 | 0.094 | 45 | 11 | 0.0239 |
| ALPL × DEFA3 × LILRA3 | 0.291 | 0.095 | 45 | 11 | 0.0272 |
| CA4 × DEFA3 × LILRA3 | 0.303 | 0.096 | 45 | 11 | 0.0393 |
| ALPL × CA4 × LILRA3 | 0.319 | 0.097 | 45 | 11 | 0.0612 |
| DEFA1 × DEFA3 × LILRA3 | 0.323 | 0.097 | 45 | 11 | 0.0678 |
| ALPL × CA4 × DEFA1 | 0.331 | 0.097 | 45 | 11 | 0.0827 |
| CA4 × DEFA1 × LILRA3 | 0.331 | 0.097 | 45 | 11 | 0.0827 |
| DEFA3 × FCGR3B × LILRA3 | 0.331 | 0.097 | 45 | 11 | 0.0827 |
| CA4 × DEFA1 × DEFA3 | 0.335 | 0.097 | 45 | 11 | 0.0910 |

TABLE 10.5

AUC of combinations of 3 urine proteins. An AUC < 0.5 indicates protein concentrations are generally lower in patients with appendicitis. P-values for the null hypothesis of AUC = 0.5 are reported.

| 3-Marker Combination | AUC | SE | ND | D | P |
|---|---|---|---|---|---|
| ALPL × CA4 × DEFA1 | 0.257 | 0.092 | 45 | 11 | 0.0079 |
| CA4 × DEFA1 × DEFA3 | 0.257 | 0.092 | 45 | 11 | 0.0079 |
| LILRA3/(CA4 × DEFA3) | 0.736 | 0.092 | 45 | 11 | 0.0105 |
| LILRA3/(ALPL × DEFA3) | 0.735 | 0.092 | 45 | 11 | 0.0109 |
| LILRA3/(ALPL × FCGR3B) | 0.732 | 0.093 | 45 | 11 | 0.0122 |
| ALPL × DEFA1 × DEFA3 | 0.273 | 0.093 | 45 | 11 | 0.0147 |
| ALPL × CA4 × DEFA3 | 0.274 | 0.093 | 45 | 11 | 0.0153 |
| ALPL × DEFA1 × FCGR3B | 0.275 | 0.093 | 45 | 11 | 0.0158 |
| ALPL × DEFA3 × FCGR3B | 0.279 | 0.094 | 45 | 11 | 0.0182 |
| LILRA3/(DEFA1 × DEFA3) | 0.721 | 0.094 | 45 | 11 | 0.0182 |
| CA4 × DEFA1 × FCGR3B | 0.285 | 0.094 | 45 | 11 | 0.0224 |
| ALPL × CA4 × FCGR3B | 0.287 | 0.094 | 45 | 11 | 0.0239 |
| CA4 × DEFA3 × FCGR3B | 0.292 | 0.095 | 45 | 11 | 0.0281 |
| LILRA3/(ALPL × CA4) | 0.707 | 0.095 | 45 | 11 | 0.0290 |
| LILRA3/(DEFA3 × FCGR3B) | 0.705 | 0.095 | 45 | 11 | 0.0309 |
| LILRA3/(ALPL × DEFA1) | 0.703 | 0.095 | 45 | 11 | 0.0328 |
| DEFA1 × DEFA3 × FCGR3B | 0.299 | 0.095 | 45 | 11 | 0.0349 |
| LILRA3/(CA4 × FCGR3B) | 0.690 | 0.096 | 45 | 11 | 0.0479 |
| LILRA3/(DEFA1 × FCGR3B) | 0.683 | 0.096 | 45 | 11 | 0.0580 |
| LILRA3/(CA4 × DEFA1) | 0.679 | 0.097 | 45 | 11 | 0.0644 |

TABLE 10.6

AUC of combinations of 3 proteins with at least 1 urine (u) and at least 1 plasma (p) protein. An AUC < 0.5 indicates protein concentrations are generally lower in patients with appendicitis. P-values for the null hypothesis of AUC = 0.5 are reported.

| 3-Marker Combination | AUC | SE | ND | D | p |
|---|---|---|---|---|---|
| DEFA1(u) × DEFA3(p) × LILRA3(p) | 0.224 | 0.088 | 45 | 11 | 0.0017 |
| DEFA1(u) × DEFA3(u) × LILRA3(p) | 0.246 | 0.091 | 45 | 11 | 0.0051 |
| DEFA1(u) × CA4(p) × DEFA3(p) | 0.246 | 0.091 | 45 | 11 | 0.0051 |
| DEFA1(u) × CA4(p) × LILRA3(p) | 0.246 | 0.091 | 45 | 11 | 0.0051 |
| DEFA1(u) × DEFA3(u) × CA4(p) | 0.253 | 0.091 | 45 | 11 | 0.0067 |
| CA4(u) × DEFA1(u) × LILRA3(p) | 0.255 | 0.091 | 45 | 11 | 0.0073 |
| DEFA1(u) × ALPL(p) × CA4(p) | 0.255 | 0.091 | 45 | 11 | 0.0073 |
| DEFA1(u) × ALPL(p) × LILRA3(p) | 0.255 | 0.091 | 45 | 11 | 0.0073 |
| CA4(u) × DEFA3(u) × LILRA3(p) | 0.261 | 0.092 | 45 | 11 | 0.0093 |
| DEFA1(u) × DEFA3(u) × ALPL(p) | 0.261 | 0.092 | 45 | 11 | 0.0093 |
| DEFA3(u) × ALPL(p) × DEFA3(p) | 0.261 | 0.092 | 45 | 11 | 0.0093 |
| ALPL(u) × DEFA1(u) × DEFA3(p) | 0.263 | 0.092 | 45 | 11 | 0.0101 |
| ALPL(u) × DEFA1(u) × LILRA3(p) | 0.265 | 0.092 | 45 | 11 | 0.0109 |
| DEFA1(u) × DEFA3(u) × DEFA3(p) | 0.265 | 0.092 | 45 | 11 | 0.0109 |
| DEFA1(u) × CA4(p) × DEFA1(p) | 0.265 | 0.092 | 45 | 11 | 0.0109 |
| ALPL(u) × FCGR3B(u) × DEFA3(p) | 0.267 | 0.093 | 45 | 11 | 0.0118 |
| DEFA1(u) × FCGR3B(u) × LILRA3(p) | 0.267 | 0.093 | 45 | 11 | 0.0118 |
| DEFA3(u) × DEFA3(p) × LILRA3(p) | 0.269 | 0.093 | 45 | 11 | 0.0127 |
| ALPL(u) × DEFA1(u) × CA4(p) | 0.271 | 0.093 | 45 | 11 | 0.0137 |
| ALPL(u) × DEFA3(u) × DEFA3(p) | 0.273 | 0.093 | 45 | 11 | 0.0147 |
| DEFA1(u) × ALPL(p) × DEFA3(p) | 0.273 | 0.093 | 45 | 11 | 0.0147 |
| ALPL(u) × FCGR3B(u) × LILRA3(p) | 0.275 | 0.093 | 45 | 11 | 0.0158 |
| CA4(u) × DEFA1(u) × CA4(p) | 0.275 | 0.093 | 45 | 11 | 0.0158 |
| ALPL(u) × FCGR3B(u) × CA4(p) | 0.277 | 0.094 | 45 | 11 | 0.0170 |
| DEFA1(u) × DEFA1(p) × LILRA3(p) | 0.277 | 0.094 | 45 | 11 | 0.0170 |
| DEFA3(u) × ALPL(p) × CA4(p) | 0.277 | 0.094 | 45 | 11 | 0.0170 |
| DEFA3(u) × CA4(p) × DEFA3(p) | 0.277 | 0.094 | 45 | 11 | 0.0170 |
| DEFA1(u) × DEFA3(u) × DEFA1(p) | 0.279 | 0.094 | 45 | 11 | 0.0182 |
| DEFA3(u) × ALPL(p) × LILRA3(p) | 0.279 | 0.094 | 45 | 11 | 0.0182 |

TABLE 10.6-continued

AUC of combinations of 3 proteins with at least 1 urine (u) and at least 1 plasma (p) protein. An AUC < 0.5 indicates protein concentrations are generally lower in patients with appendicitis. P-values for the null hypothesis of AUC = 0.5 are reported.

| 3-Marker Combination | AUC | SE | ND | D | p |
|---|---|---|---|---|---|
| ALPL(u) × DEFA1(u) × ALPL(p) | 0.281 | 0.094 | 45 | 11 | 0.0195 |
| CA4(u) × DEFA1(u) × DEFA3(p) | 0.281 | 0.094 | 45 | 11 | 0.0195 |
| ALPL(u) × FCGR3B(u) × ALPL(p) | 0.283 | 0.094 | 45 | 11 | 0.0209 |
| CA4(u) × DEFA3(u) × DEFA3(p) | 0.283 | 0.094 | 45 | 11 | 0.0209 |
| FCGR3B(u) × DEFA3(p) × LILRA3(p) | 0.283 | 0.094 | 45 | 11 | 0.0209 |
| ALPL(u) × DEFA1(u) × DEFA1(p) | 0.285 | 0.094 | 45 | 11 | 0.0224 |
| ALPL(u) × DEFA3(p) × LILRA3(p) | 0.285 | 0.094 | 45 | 11 | 0.0224 |
| CA4(u) × DEFA3(u) × CA4(p) | 0.289 | 0.095 | 45 | 11 | 0.0255 |
| ALPL(u) × CA4(p) × DEFA3(p) | 0.291 | 0.095 | 45 | 11 | 0.0272 |
| DEFA3(u) × CA4(p) × LILRA3(p) | 0.291 | 0.095 | 45 | 11 | 0.0272 |
| ALPL(u) × ALPL(p) × DEFA3(p) | 0.293 | 0.095 | 45 | 11 | 0.0290 |
| CA4(u) × DEFA1(u) × ALPL(p) | 0.293 | 0.095 | 45 | 11 | 0.0290 |
| CA4(u) × FCGR3B(u) × LILRA3(p) | 0.294 | 0.095 | 45 | 11 | 0.0299 |
| ALPL(u) × CA4(u) × DEFA3(p) | 0.295 | 0.095 | 45 | 11 | 0.0309 |
| ALPL(u) × DEFA3(u) × LILRA3(p) | 0.295 | 0.095 | 45 | 11 | 0.0309 |
| DEFA3(u) × FCGR3B(u) × LILRA3(p) | 0.295 | 0.095 | 45 | 11 | 0.0309 |
| ALPL(u) × FCGR3B(u) × DEFA1(p) | 0.299 | 0.095 | 45 | 11 | 0.0349 |
| ALPL(u) × CA4(u) × CA4(p) | 0.301 | 0.095 | 45 | 11 | 0.0370 |
| ALPL(u) × DEFA3(u) × ALPL(p) | 0.301 | 0.095 | 45 | 11 | 0.0370 |
| CA4(u) × DEFA3(u) × ALPL(p) | 0.301 | 0.095 | 45 | 11 | 0.0370 |
| CA4(u) × FCGR3B(u) × DEFA3(p) | 0.301 | 0.095 | 45 | 11 | 0.0370 |
| DEFA1(u) × DEFA1(p) × DEFA3(p) | 0.301 | 0.095 | 45 | 11 | 0.0370 |
| DEFA3(u) × FCGR3B(u) × DEFA3(p) | 0.301 | 0.095 | 45 | 11 | 0.0370 |
| DEFA3(u) × CA4(p) × DEFA1(p) | 0.301 | 0.095 | 45 | 11 | 0.0370 |
| DEFA3(u) × DEFA1(p) × LILRA3(p) | 0.301 | 0.095 | 45 | 11 | 0.0370 |
| DEFA1(u) × FCGR3B(u) × CA4(p) | 0.305 | 0.096 | 45 | 11 | 0.0416 |
| DEFA3(u) × FCGR3B(u) × ALPL(p) | 0.305 | 0.096 | 45 | 11 | 0.0416 |
| DEFA3(u) × DEFA1(p) × DEFA3(p) | 0.305 | 0.096 | 45 | 11 | 0.0416 |
| DEFA3(u) × FCGR3B(p) × LILRA3(p) | 0.306 | 0.096 | 45 | 11 | 0.0428 |
| ALPL(u) × CA4(u) × LILRA3(p) | 0.307 | 0.096 | 45 | 11 | 0.0441 |
| CA4(u) × DEFA3(p) × LILRA3(p) | 0.307 | 0.096 | 45 | 11 | 0.0441 |
| ALPL(u) × DEFA3(u) × CA4(p) | 0.309 | 0.096 | 45 | 11 | 0.0466 |
| ALPL(u) × ALPL(p) × LILRA3(p) | 0.309 | 0.096 | 45 | 11 | 0.0466 |
| DEFA3(u) × FCGR3B(u) × CA4(p) | 0.309 | 0.096 | 45 | 11 | 0.0466 |
| ALPL(u) × CA4(p) × LILRA3(p) | 0.311 | 0.096 | 45 | 11 | 0.0493 |
| DEFA3(u) × ALPL(p) × DEFA1(p) | 0.311 | 0.096 | 45 | 11 | 0.0493 |
| FCGR3B(u) × ALPL(p) × LILRA3(p) | 0.311 | 0.096 | 45 | 11 | 0.0493 |
| ALPL(u) × CA4(u) × ALPL(p) | 0.313 | 0.096 | 45 | 11 | 0.0521 |
| DEFA3(u) × FCGR3B(u) × DEFA1(p) | 0.313 | 0.096 | 45 | 11 | 0.0521 |
| ALPL(u) × DEFA1(u) × FCGR3B(p) | 0.315 | 0.096 | 45 | 11 | 0.0550 |
| DEFA1(u) × FCGR3B(p) × LILRA3(p) | 0.315 | 0.096 | 45 | 11 | 0.0550 |
| FCGR3B(u) × DEFA1(p) × LILRA3(p) | 0.315 | 0.096 | 45 | 11 | 0.0550 |
| FCGR3B(u) × ALPL(p) × DEFA3(p) | 0.315 | 0.096 | 45 | 11 | 0.0550 |
| CA4(u) × DEFA3(u) × DEFA1(p) | 0.317 | 0.096 | 45 | 11 | 0.0580 |
| DEFA1(u) × ALPL(p) × DEFA1(p) | 0.317 | 0.096 | 45 | 11 | 0.0580 |
| ALPL(u) × ALPL(p) × CA4(p) | 0.319 | 0.097 | 45 | 11 | 0.0612 |
| DEFA1(u) × DEFA3(u) × FCGR3B(p) | 0.319 | 0.097 | 45 | 11 | 0.0612 |
| FCGR3B(u) × CA4(p) × LILRA3(p) | 0.319 | 0.097 | 45 | 11 | 0.0612 |
| LILRA3(u)/(DEFA1(p) × LILRA3(p)) | 0.681 | 0.097 | 45 | 11 | 0.0612 |
| ALPL(u) × FCGR3B(p) × LILRA3(p) | 0.321 | 0.097 | 45 | 11 | 0.0644 |
| CA4(u) × CA4(p) × LILRA3(p) | 0.323 | 0.097 | 45 | 11 | 0.0678 |
| DEFA1(u) × FCGR3B(u) × ALPL(p) | 0.323 | 0.097 | 45 | 11 | 0.0678 |
| FCGR3B(u) × CA4(p) × DEFA3(p) | 0.323 | 0.097 | 45 | 11 | 0.0678 |
| DEFA3(u) × CA4(p) × FCGR3B(p) | 0.325 | 0.097 | 45 | 11 | 0.0714 |
| ALPL(u) × FCGR3B(u) × FCGR3B(p) | 0.326 | 0.097 | 45 | 11 | 0.0732 |
| ALPL(u) × DEFA1(p) × LILRA3(p) | 0.327 | 0.097 | 45 | 11 | 0.0750 |
| DEFA1(u) × FCGR3B(u) × DEFA3(p) | 0.327 | 0.097 | 45 | 11 | 0.0750 |
| ALPL(u) × DEFA1(p) × DEFA3(p) | 0.329 | 0.097 | 45 | 11 | 0.0788 |
| CA4(u) × DEFA1(u) × DEFA1(p) | 0.329 | 0.097 | 45 | 11 | 0.0788 |
| CA4(u) × FCGR3B(u) × CA4(p) | 0.329 | 0.097 | 45 | 11 | 0.0788 |
| CA4(u) × DEFA3(u) × FCGR3B(p) | 0.332 | 0.097 | 45 | 11 | 0.0848 |
| ALPL(u) × DEFA3(u) × DEFA1(p) | 0.333 | 0.097 | 45 | 11 | 0.0868 |
| DEFA1(u) × DEFA3(p) × FCGR3B(p) | 0.333 | 0.097 | 45 | 11 | 0.0868 |
| ALPL(u) × CA4(u) × DEFA1(p) | 0.335 | 0.097 | 45 | 11 | 0.0910 |
| DEFA3(u) × DEFA3(p) × FCGR3B(p) | 0.335 | 0.097 | 45 | 11 | 0.0910 |
| ALPL(u) × CA4(p) × DEFA1(p) | 0.337 | 0.098 | 45 | 11 | 0.0954 |
| ALPL(u) × DEFA3(p) × FCGR3B(p) | 0.337 | 0.098 | 45 | 11 | 0.0954 |
| CA4(u) × FCGR3B(u) × ALPL(p) | 0.337 | 0.098 | 45 | 11 | 0.0954 |
| DEFA1(u) × CA4(p) × FCGR3B(p) | 0.337 | 0.098 | 45 | 11 | 0.0954 |
| FCGR3B(u) × ALPL(p) × CA4(p) | 0.337 | 0.098 | 45 | 11 | 0.0954 |
| ALPL(u) × DEFA3(u) × FCGR3B(p) | 0.338 | 0.098 | 45 | 11 | 0.0976 |
| ALPL(u) × ALPL(p) × DEFA1(p) | 0.339 | 0.098 | 45 | 11 | 0.0999 |
| FCGR3B(u) × DEFA1(p) × DEFA3(p) | 0.339 | 0.098 | 45 | 11 | 0.0999 |

TABLE 11.1

Confusion table and odds ratio for appendicitis using plasma protein combination ALPL × DEFA3. A cutoff concentration of 1526 $(ng/mL)^2$ is selected corresponding to the 50th percentile.

| ALPL × DEFA3 | Adjudication | | |
|---|---|---|---|
| | ABD | Appy | Total |
| <=cutoff | 18 | 10 | 28 |
| >cutoff | 27 | 1 | 28 |
| Total | 45 | 11 | 56 |

Odds ratio (95% CI)=15.0 (2.2-98.3), where Odds ratio=Odds below cutoff/Odds above cutoff.

TABLE 11.2

Confusion table and odds ratio for appendicitis using urine protein combination ALPL × DEFA1. A cutoff concentration of 50.7 $(ng/mL)^2$ is selected corresponding to the 60th percentile.

| ALPL × DEFA1 | Adjudication | | |
|---|---|---|---|
| | ABD | Appy | Total |
| <=cutoff | 24 | 10 | 34 |
| >cutoff | 21 | 1 | 22 |
| Total | 45 | 11 | 56 |

Odds ratio (95% CI)=8.8 (1.3-57.2), where Odds ratio=Odds below cutoff/Odds above cutoff.

TABLE 11.3

Confusion table and odds ratio for appendicitis using DEFA1(u) × DEFA3(p) × LILRA3(p). A cutoff concentration of 3.97 $(ng/mL)^3$ is selected corresponding to the 50th percentile.

| DEFA1(u) × DEFA3(p) × LILRA3(p) | Adjudication | | |
|---|---|---|---|
| | ABD | Appy | Total |
| <=cutoff | 19 | 9 | 28 |
| >cutoff | 26 | 2 | 28 |
| Total | 45 | 11 | 56 |

Odds ratio (95% CI)=6.2 (1.3-28.3), where Odds ratio=Odds below cutoff/Odds above cutoff.

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A method of diagnosing and treating appendicitis comprising:
   (a) performing an assay for measuring a level or a concentration of Defensin alpha 3 protein in a body fluid sample obtained from a human patient presenting with symptoms that mimic appendicitis,
   (b) comparing the level or concentration of Defensin alpha 3 protein with a threshold, wherein the threshold is a level or concentration of the Defensin alpha 3 protein in a body fluid sample obtained from a control population of human subjects having symptoms that mimic appendicitis and not having appendicitis, wherein the body fluid for the patient is the same as the body fluid obtained from the control population of human subjects,
   (c) diagnosing the patient with appendicitis when the level of Defensing alpha 3 in the body fluid sample obtained from the patient is decreased as compared to the threshold; and
   (d) treating the diagnosed patient of (c) wherein the treatment comprises performing an appendectomy,
   wherein the body fluid sample is selected from the group consisting of blood, serum, and plasma and urine.

2. The method according to claim 1, wherein method provides a sensitivity or specificity of at least 0.7 for diagnosing the patient with appendicitis.

3. A method according to claim 1, wherein the sample is selected from the group consisting of blood, serum, and plasma.

* * * * *

UNITED STATES PATENT AND TRADEMARK OFFICE
CERTIFICATE OF CORRECTION

PATENT NO. : 11,371,096 B2
APPLICATION NO. : 15/521213
DATED : June 28, 2022
INVENTOR(S) : Lakhmir S. Chawla and Timothy A. McCaffrey It is certified that error appears in the above-identified patent and that said Letters Patent is hereby corrected as shown below:

In the Claims

Column 50, Line 16, cancel the text beginning with "1. A method of diagnosing and treating appendicitis" to and ending "plasma and urine." in Column 50, Line 38, and insert the following:
--1. A method of diagnosing and treating appendicitis comprising:
(a) performing an assay for measuring a level of Defensin alpha 3 mRNA in a blood sample obtained from a human patient with abdominal pain,
(b) comparing the measured level of Defensin alpha 3 mRNA with a threshold level, wherein the threshold level is Defensin alpha 3 mRNA measured in blood from a control population of human subjects having abdominal pain and not having appendicitis,
(c) determining the human patient has decreased Defensin alpha 3 mRNA as compared to the threshold level and diagnosing the human patient with appendicitis; and
(d) treating the human patient diagnosed with appendicitis by performing an appendectomy.--

Column 50, Line 42, cancel the text beginning with "3. A method according to claim 1, wherein the sample is" to and ending in "plasma." in Column 50, Line 44, and insert the following:
--3. A method according to claim 1, wherein the blood sample is selected from the group consisting of serum and plasma.--

Signed and Sealed this
Eighteenth Day of October, 2022

Katherine Kelly Vidal
*Director of the United States Patent and Trademark Office*